US008030436B2

(12) United States Patent
Pacetti et al.

(10) Patent No.: US 8,030,436 B2
(45) Date of Patent: Oct. 4, 2011

(54) POLY(ESTER-AMIDE) ELASTOMERS AND THEIR USE WITH IMPLANTABLE MEDICAL DEVICES

(75) Inventors: Stephen Dirk Pacetti, San Jose, CA (US); Jessica Reneé DesNoyer, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1245 days.

(21) Appl. No.: 11/487,059

(22) Filed: Jul. 13, 2006

(65) Prior Publication Data

US 2008/0014236 A1    Jan. 17, 2008

(51) Int. Cl.
*C08G 69/26* (2006.01)
*C08G 69/28* (2006.01)

(52) U.S. Cl. ......... 528/332; 528/335; 528/336; 528/339

(58) Field of Classification Search ............... None
See application file for complete search history.

(56) References Cited

U.S. PATENT DOCUMENTS

| | | | |
|---|---|---|---|
| 4,304,767 A | 12/1981 | Heller et al. | |
| 4,733,665 A | 3/1988 | Palmaz | |
| 4,800,882 A | 1/1989 | Gianturco | |
| 4,886,062 A | 12/1989 | Wiktor | |
| 5,581,387 A | 12/1996 | Cahill | |
| 5,861,387 A | 1/1999 | Labrie et al. | |
| 6,503,538 B1 * | 1/2003 | Chu et al. ................ | 424/497 |
| 6,703,040 B2 | 3/2004 | Katsarava et al. | |
| 7,056,591 B1 | 6/2006 | Pacetti et al. | |
| 2005/0245637 A1 | 11/2005 | Hossainy et al. | |
| 2005/0266038 A1 * | 12/2005 | Glauser et al. ............. | 424/423 |

FOREIGN PATENT DOCUMENTS

| | | |
|---|---|---|
| WO | WO 02/18477 | 3/2002 |
| WO | WO 2005/121250 | 12/2005 |

OTHER PUBLICATIONS

R.R. Roesler & K. Danielmeier, "Tris-3-(1-aziridino)propionates and their use in formulated products", Prog. Org. Coat., 2004, 50(1), pp. 1-27.*

International Search Rep. for PCT/US2007/015902, filed Jul. 12, 2007, mailed Nov. 30, 2007, 11 pgs.
U.S. Appl. No. 10/718,278, filed Nov. 19, 2003, Hossainy et al.
U.S. Appl. No. 10/719,516, filed Nov. 21, 2003, Tang et al.
U.S. Appl. No. 10/738,704, filed Dec. 16, 2003, Pacetti et al.
U.S. Appl. No. 10/741,214, filed Dec. 19, 2003, Pacetti et al.
U.S. Appl. No. 10/750,139, filed Dec. 30, 2003, DesNoyer et al.
U.S. Appl. No. 10/805,036, filed Mar. 16, 2004, Pacetti.
U.S. Appl. No. 10/816,072, filed Mar. 31, 2004, Dugan et al.
U.S. Appl. No. 10/835,656, filed Apr. 30, 2004, Tang et al.
U.S. Appl. No. 10/855,294, filed May 26, 2004, Pacetti et al.
U.S. Appl. No. 10/960,381, filed Oct. 6, 2004, DesNoyer et al.
U.S. Appl. No. 10/975,247, filed Oct. 27, 2004, DesNoyer et al.
U.S. Appl. No. 10/976,551, filed Oct. 29, 2004, DesNoyer et al.
U.S. Appl. No. 10/999,391, filed Nov. 29, 2004, Hossainy.
U.S. Appl. No. 11/023,837, filed Dec. 27, 2004, Hossainy.
U.S. Appl. No. 11/027,955, filed Dec. 30, 2004, Hossainy et al.
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
De Lezo et al., *Intracoronary Ultrasound Assessment of Directional Coronary Atherectomy: Immediate and Follow-Up Findings*, JACC vol. 21, No. 2, (1993) pp. 298-307.
Moreno et al., *Macrophage Infiltration Predicts Restenosis After Coronary Intervention in Patients with Unstable Angina*, Circulation, vol. 94, No. 12, (1996) pp. 3098-3102.
Oikawa et al., Mechanisms of Acute Gain and Late Lumen Loss After Atherectomy in Different Preintervention Arterial Remodeling Patterns, The Am. J. of Cardilogy, vol. 89, (2002) pp. 505-510.
Scully et al., *Effect of a heparan sulphate with high affinity for antithrombin III upon inactivation of thrombin and coagulaton Factor Xa*, Biochem J. 262, (1989) pp. 651-658.
Virmani et al., *Lessons From Sudden Coronary Death a Comprehensive Morphological Classification Scheme for Atherosclerotic Lesions*, Arterioscler Thromb Vasc Biol. (2000) pp. 1262-1275.

* cited by examiner

*Primary Examiner* — Frederick Krass
*Assistant Examiner* — Brian Gulledge
(74) *Attorney, Agent, or Firm* — Squire, Sanders & Dempsey (US) LLP

(57) ABSTRACT

The present invention relates to implantable medical devices comprising poly(ester-amide) elastomers in coating layers on the device.

45 Claims, No Drawings

POLY(ESTER-AMIDE) ELASTOMERS AND THEIR USE WITH IMPLANTABLE MEDICAL DEVICES

FIELD

This invention relates to the fields of organic chemistry, polymer chemistry, materials science, and medical devices.

BACKGROUND

Until the mid-1980s, the accepted treatment for atherosclerosis, i.e., narrowing of the coronary artery(ies) was coronary by-pass surgery. While effective and having evolved to a relatively high degree of safety for such an invasive procedure, by-pass surgery still involves potentially serious complications and in the best of cases an extended recovery period.

With the advent of percutaneous tranluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it other problems such as vasospasm and elastic recoil of the stretched arterial wall which could undo much of what was accomplished and, in addition, it created a new disease, restenosis, the re-clogging of the treated artery due to neointimal hyperplasia.

The next improvement, advanced in the mid-1980s was the use of a stent to maintain the luminal diameter after PTCA. This for all intents and purposes put an end to vasospasm and elastic recoil but did not entirely resolve the issue of restenosis. That is, prior to the introduction of stents, restenosis occurred in from 30-50% of patients undergoing PTCA. Stenting reduced this to about 15-20%, much improved but still more than desirable.

In 2003, drug-eluting stents or DESs were introduced. The drugs initially employed with the DES were cytostatic compounds, compounds that curtailed the proliferation of cells that resulted in restenosis. The occurrence of restenosis was thereby reduced to about 5-7%, a relatively acceptable figure. Today, the DES is the default the industry standard to treatment of atherosclerosis and is rapidly gaining favor for treatment of stenoses of blood vessels other than coronary arteries such as peripheral angioplasty of the femoral artery.

One of the key criteria of DESs is selection of a polymer or blend of polymers to be used in a drug reservoir layer, a rate-controlling layer, a protective topcoat layer, etc. If a biostable polymer is selected, i.e., a polymer that does not significantly decompose in a patient's body, their chemical composition is often not of significant concern since they are not intended to break down and enter the patient's system. On the other hand, currently biodegradable polymers are preferred for many applications because their ability to decompose in a biological environment confers on them a number of desirable characteristics. For example, the fact that a polymer will biodegrade and can eventually be essentially completely eliminated from a patient's body can avoid the need to invasively remove a DES after its job is done. In addition, by judicious choice of biodegradable polymer, e.g., selecting one that bio-erodes by bulk erosion or one that bio-erodes by surface erosion, the properties of the polymer can be used as an added tool for the fine-tuning of the release rate of a drug.

Of course, if a polymer is going to degrade in a patient's body, it is imperative that it be biocompatible, that is, that its degradation products do no harm to the patient. This requires careful attention to the chemistry of the polymer and the properties of its degradation products. A great deal of work has gone into the effort to find suitable biodegradable polymers and one class of such polymers that is exhibiting particularly desirable properties in terms of biodegradation, biocompatibility, drug compatibility and, generally, the range of properties that can be engineered into the polymer by judicious selection their constitutional units is the poly(ester-amide) family of polymers.

As currently employed, however, poly(ester-amide)s tend generally to be rather soft and quite permeable to many if not most drugs, which limits their application in DESs to some extent. What is needed is poly(ester-amide)s that are stronger, tougher and less permeable than those currently in use while still maintaining the other beneficial characteristics of the class. The current invention provides such poly(ester-amide)s and methods of their use.

SUMMARY

The current invention is directed to elastomeric poly(ester-amide)s and their use.

Thus, in one aspect, the present invention relates to a poly (ester-amide) having the formula:

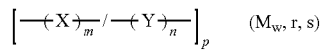

wherein:
m is an integer from 0 to about 200;
n is an integer from 0 to about 200;
p is an integer from 1 to about 3000;
$M_n$ is from about 10,000 to about 1,000,000 Da.
r is a number from 0 to 1, inclusive;
s is a number from 0 to 1, inclusive;
r+s=1;
X has the chemical structure:

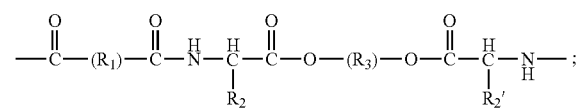

Y has the chemical structure:

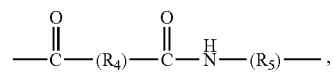

wherein:
$R_5$ is selected from the group consisting of:

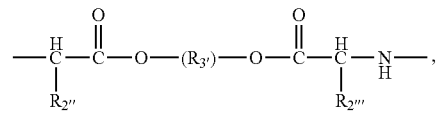

—CH(COR$_6$)CH$_2$S—, —CH(COR$_6$)CH$_2$O—, —CH(COR$_6$)(CH$_2$)$_4$NH—, —(CH$_2$)$_4$CH(COR$_6$)NH—, —CH(COR$_6$)CH(CH$_3$)O—,

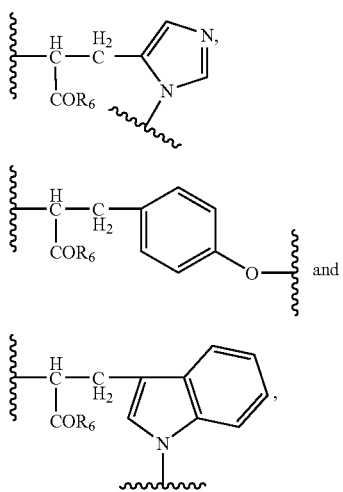

wherein:

R$_6$ is selected from the group consisting of —OH, —O(1C-20C)alkenyl and —O(CH$_2$CH$_2$O)$_q$CH$_2$CH$_2$OR$_7$, wherein:

q is an integer from 1 to 600, inclusive;

R$_7$ is selected from the group consisting of —C(O)CH═CH$_2$ and —C(O)C(CH$_3$)═CH$_2$;

R$_1$ and R$_4$ are independently selected from the group consisting of (1C-12C)alkyl and (2C-12C)alkenyl;

R$_2$, R$_{2'}$, R$_{2''}$ and R$_{2'''}$ are independently selected from the group consisting of hydrogen and (1C-4C)alkyl, wherein:

the alkyl group is optionally substituted with a moiety selected from the group consisting of —OH, —SH, —SeH, —C(O)OH, —NHC(NH)NH$_2$,

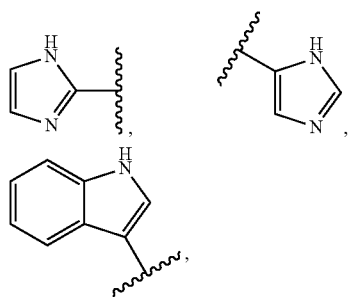

phenyl and

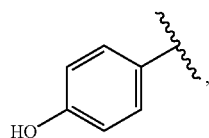

or one or more of R$_2$, R$_{2'}$, R$_{2''}$ and R$_{2'''}$ may form a bridge between the carbon to which it is attached and the adjacent nitrogen, the bridge comprising —CH$_2$CH$_2$CH$_2$—;

R$_3$ and R$_{3'}$ are independently selected from the group consisting of (1C-12C)alkyl, (2C-12C)alkenyl, (3C-8C)cycloalkyl and —(CH$_2$CH$_2$O)$_q$CH$_2$CH$_2$—, wherein q is an integer from 1 to 10, inclusive, wherein the poly(ester-amide) is from about 0.05 mol % to about 5 mol % cross-linked.

In an aspect of this invention, $M_n$ is from about 20,000 Da to about 500,000 Da.

In an aspect of this invention, the crosslink is a chemical crosslink.

In an aspect of this invention, the chemical crosslink comprises a reaction product of an —OH, —SH, —NH$_2$ or —C(O)OH substituent on R$_2$, R$_{2'}$, R$_{2''}$, R$_{2'''}$ or R$_6$ with a multifunctional OH-reactive, —SH-reactive, —NH$_2$-reactive or —C(O)OH-reactive multifunctional crosslinking agent.

In an aspect of this invention, the OH-reactive, —SH-reactive, —NH$_2$-reactive or —C(O)OH-reactive multifunctional crosslinking agent comprises a diisocyanate.

In an aspect of this invention, the diisocyanate is selected from the group consisting of 1,2-ethanediisocyanate, 1,3-propanediisocyanate, 1,4-butanediisocyanate, 1,5-pentanediisocyanate, lysine diisocyanate and 1,4-cyclohexanediisocyanate.

In an aspect of this invention, the —SH-reactive multifunctional crosslinking agent comprises a bismaleimide.

In an aspect of this invention, the —OH-reactive, —SH-reactive, NH$_2$-reactive or —C(O)OH-reactive multifunctional crosslinking agent comprises a diepoxide.

In an aspect of this invention, the —OH-reactive, —SH-reactive, —NH$_2$-reactive or —C(O)OH-reactive multifunctional crosslinking agent comprises a diisothiocyanate.

In an aspect of this invention, the —OH-reactive, —SH-reactive, —NH$_2$-reactive or —C(O)OH-reactive multifunctional crosslinking agent comprises a diacid halide.

In an aspect of this invention, R$_2$, R$_{2'}$, R$_{2''}$ and R$_{2'''}$ are independently selected from the group consisting of unsubstituted (1C-4C)alkyl and a bridge between the carbon to which it is attached and the adjacent nitrogen, the bridge comprising —CH$_2$CH$_2$CH$_2$—;

R$_5$ is selected from the group consisting of —CH(COR$_6$)CH$_2$S—, —CH(COR$_6$)CH$_2$O—, —CH(COR$_6$)(CH$_2$)$_4$NH—, —(CH$_2$)$_4$CH(COR$_6$)NH—, —CH(COR$_6$)CH(CH$_3$)O—,

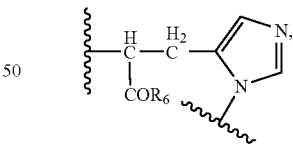

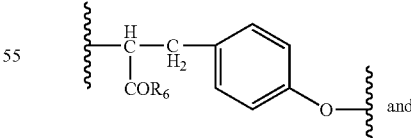

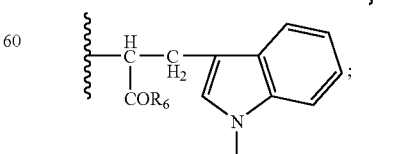

and, $R_6$ is —OH.

In an aspect of this invention, $R_5$ is —$(CH_2)_4CH(COR_6)NH$—.

In an aspect of this invention, $R_2$ and $R_{2'}$ are —$CH_2CH(CH_3)_2$.

In an aspect of this invention, the OH-reactive, SH-reactive, $NH_2$ reactive, C(O)OH-reactive multifunctional crosslinking agent is a multifunctional aziridine compound.

In an aspect of this invention, the multifunctional aziridine compound is pentaerythriol tris(3-aziridinopropionate).

In an aspect of this invention, $R_2$, $R_{2'}$, $R_{2''}$ and $R_{2'''}$ are independently selected from the group consisting of unsubstituted (1C-4C)alkyl and a bridge between the carbon to which it is attached and the adjacent nitrogen, the bridge comprising —$CH_2CH_2CH_2$—;

$R_5$ is selected from the group consisting of —$CH(COR_6)CH_2S$—, —$CH(COR_6)CH_2O$—, —$CH(COR_6)(CH_2)_4NH$—, —$(CH_2)_4CH(COR_6)NH$—, —$CH(COR_6)CH(CH_3)O$—,

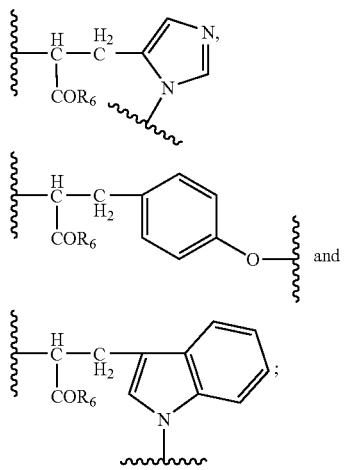

and, $R_6$ is —OH.

In an aspect of this invention, $R_5$ is —$(CH_2)_4CH(COR_6)NH$—.

In an aspect of this invention, $R_2$ and $R_{2'}$ are —$CH_2CH(CH_3)_2$.

In an aspect of this invention, $R_1$ and $R_4$ are —$(CH_2)_8$—; and, $R_3$ is —$(CH_2)_6$—.

In an aspect of this invention, $R_5$ is selected from the group consisting of

—$CH(COR_6)CH_2S$—, —$CH(COR_6)CH_2O$—, —$CH(COR_6)(CH_2)_4NH$—, —$(CH_2)_4CH(COR_6)NH$—, —$CH(COR_6)CH(CH_3)O$—,

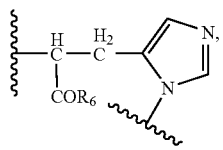

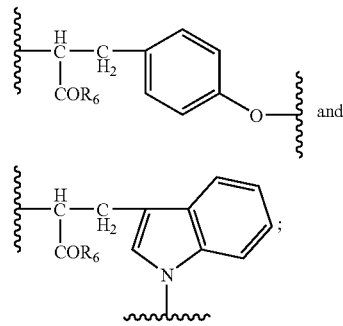

$R_6$ is selected from the group consisting of —$O(1C-20C)$alkenyl and —$O(CH_2CH_2O)_qCH_2CH_2OR_7$, wherein:
q is an integer from 0 to 600, inclusive;
$R_7$ is selected from the group consisting of —$C(O)CH=CH_2$ and —$C(O)C(CH_3)=CH_2$; and,
the chemical crosslink comprises UV or free-radical initiated reaction of the double bond.

In an aspect of this invention, in the aspect just above, $R_5$ is —$(CH_2)_4CH(COR_6)NH$—.

In an aspect of this invention, in the aspect just above, $R_6$ is selected from the group consisting of —$O(CH_2)_8CH=CH(CH_2)_7CH_3$ and

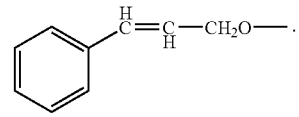

In an aspect of this invention, $R_1$ and $R_4$ are —$(CH_2)_8$—; $R_2$ and $R_{2'}$ are —$CH_2CH(CH_3)_2$ and $R_3$ is —$(CH_2)_6$.

In an aspect of this invention, m is 0.75; and, n is 0.25.

In an aspect of this invention, $R_5$ is

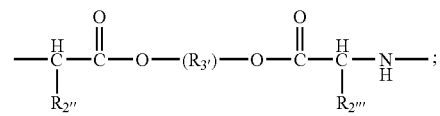

one of $R_1$ or $R_4$ is a (2C-12C)alkyenyl, the other is a (1C-12C)alkyl; or, $R_1$ and $R_4$ are a (2C-12C)alkyenyl and the chemical crosslink comprises UV or free-radical initiated reaction of the alkenyl double bond.

In an aspect of this invention, n is 0; $R_1$ is a (2C-12C)alkenyl; and, the chemical crosslink comprises UV or free-radical initiated reaction of the alkenyl double bond.

In an aspect of this invention, $R_2$ and $R_{2'}$ are —$(CH_2)CH(CH_3)_2$; and, $R_3$ is —$(CH_2)_6$—.

In an aspect of this invention, at least one of $R_2$, $R_{2'}$, $R_{2''}$, $R_{2'''}$ and $R_6$ comprises a —C(O)OH group; and the chemical crosslink comprises an ionomer.

In an aspect of this invention, the ionomer comprises a monovalent cation.

In an aspect of this invention, the monovalent cation is selected from the group consisting of sodium, potassium, lithium and silver.

In an aspect of this invention the ionomer comprises a polyvalent cation.

In an aspect of this invention, the polyvalent cation is selected from the group consisting of calcium(II), magnesium(II), zinc(II), iron(II) and aluminum(III).

In an aspect of this invention, $R_2$ and $R_{2'}$ are independently selected from the group consisting of hydrogen and (1C-4C) alkyl;

$R_5$ is selected from the group consisting of —CH(COR$_6$)CH$_2$S—, —CH(COR$_6$)CH$_2$O—, —CH(COR$_6$)(CH$_2$)$_4$NH—, —(CH$_2$)$_4$CH(COR$_6$)NH—, —CH(COR$_6$)CH(CH$_3$)O—,

[structures showing histidyl, tyrosyl, and tryptophyl side chain moieties with COR$_6$ groups]

and,
$R_6$ is —OH.

In an aspect of this invention, in the aspect just above, $R_2$ and $R_{2'}$ are —CH$_2$CH(CH$_3$)$_2$; and $R_5$ is —(CH$_2$)$_4$CH(COR$_6$)NH—.

In an aspect of this invention, in the aspect just above, $R_1$ and $R_4$ are —(CH$_2$)$_8$—; $R_3$ is —(CH$_2$)$_6$—.

In an aspect of this invention, the ionomer herein comprises Zn(II).

In an aspect of this invention, the cross-link is a physical crosslink.

In an aspect of this invention, where the cross-link is physical, A is a soft segment; B is a hard segment; and, the physical crosslink comprises segregated domains of soft segments and paracrystalline hard segments.

In an aspect of this invention A has a glass-transition temperature of 40° C. of lower; and, B has a glass transition temperature of 45° C. or higher.

In an aspect of this invention $R_5$ is

[structure: —CH(R$_{2''}$)—C(=O)—O—(R$_{3'}$)—O—C(=O)—CH(R$_{2'''}$)—NH—]

In an aspect of this invention $R_1$ is —(CH$_2$)$_8$—; $R_2$ and $R_{2'}$ are —(CH(CH$_3$)CH$_2$CH$_3$; $R_3$ is —(CH$_2$)$_6$—; $R_{1'}$ is —(CH$_2$)$_4$—; $R_{2''}$ and $R_{2'''}$ are —CH(CH$_3$)$_2$ and $R_{3'}$ is —(CH$_2$)$_3$—.

In an aspect of this invention, $R_1$ is —(CH$_2$)$_4$—; $R_2$ and $R_{2'}$ are —CH(CH$_3$)CH$_2$CH$_3$; $R_3$ is —(CH$_2$)$_{12}$—; $R_{1'}$ is —(CH$_2$)$_4$—; $R_{2''}$ and $R_{2'''}$ are —CH(CH$_3$)$_2$ and $R_{3'}$ is —(CH$_2$)$_3$—.

In an aspect of this invention, $R_1$ is —(CH$_2$)$_8$—; $R_2$, $R_{2'}$, $R_{2''}$ and $R_{2'''}$ are —(CH(CH$_3$)CH$_2$CH$_3$; $R_3$ is —(CH$_2$)$_6$—; $R_{1'}$ is —(CH$_2$)$_2$— and $R_{3'}$ is —(CH$_2$)$_2$—.

In an aspect of this invention, A is amorphous; B is crystalline; and the crosslink comprises inter-chain crystallization.

In an aspect of this invention, where A is amorphous and B is crystalline, $R_5$ is

[structure: —CH(R$_{2''}$)—C(=O)—O—(R$_{3'}$)—O—C(=O)—CH(R$_{2'''}$)—NH—]

In an aspect of this invention, where A is amorphous and B is crystalline, $R_1$ is —(CH$_2$)$_8$—; $R_{1'}$ is —(CH$_2$)$_4$—; $R_2$ and $R_{2'}$ are —CH$_2$CH(CH$_3$)$_2$; $R_{2''}$ and $R_{2'''}$ are CH$_2$ phenyl; $R_3$ is —(CH$_2$)$_6$—; and, $R_{3'}$ is —(CH$_2$)$_4$—.

An aspect of this invention is an implantable medical device, comprising:
a device body; an optional primer layer; a drug reservoir layer comprising at least one therapeutic agent; an optional rate-controlling layer; and an optional topcoat layer; wherein at least one of the drug reservoir layer, the rate-controlling layer, if opted, and/or the topcoat layer, if opted, comprises a poly (ester-amide) of this invention wherein the poly(ester-amide) has the formula:

$$\left[ -(X)_{\overline{m}}/-(Y)_{\overline{n}} \right]_p \quad (M_w, r, s)$$

wherein:
m is an integer from 0 to about 200;
n is an integer from 0 to about 200;
p is an integer from 1 to about 3000;
$M_w$ is from about 10,000 to about 1,000,000 Da.
r is a number from 0 to 1, inclusive;
s is a number from 0 to 1, inclusive;
r+s=1;
X has the chemical structure:

[structure: —C(=O)—(R$_1$)—C(=O)—NH—CH(R$_2$)—C(=O)—O—(R$_3$)—O—C(=O)—CH(R$_{2'}$)—NH—]

Y has the chemical structure:

[structure: —C(=O)—(R$_4$)—C(=O)—NH—(R$_5$)—]

wherein:
$R_5$ is selected from the group consisting of:

[structure: —CH(R$_{2''}$)—C(=O)—O—(R$_{3'}$)—O—C(=O)—CH(R$_{2'''}$)—NH—],

—CH(COR$_6$)CH$_2$S—, —CH(COR$_6$)CH$_2$O—, —CH(COR$_6$)(CH$_2$)$_4$NH—, —(CH$_2$)$_4$CH(COR$_6$)NH—, —CH(COR$_6$)CH(CH$_3$)O—,

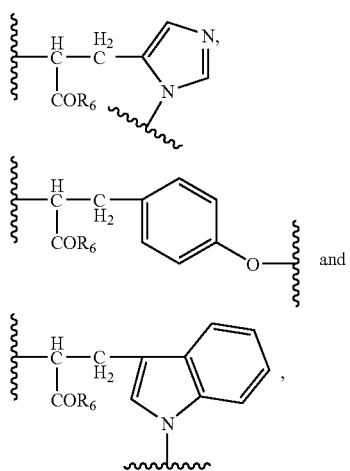

wherein:
R$_6$ is selected from the group consisting of —OH, —O(1C-20C)alkenyl and —O(CH$_2$CH$_2$O)$_q$CH$_2$CH$_2$OR$_7$, wherein:
q is an integer from 1 to 600, inclusive;
R$_7$ is selected from the group consisting of —C(O)CH=CH$_2$ and —C(O)C(CH$_3$)=CH$_2$;
R$_1$ and R$_4$ are independently selected from the group consisting of (1C-12C)alkyl and (2C-12C)alkenyl;
R$_2$, R$_{2'}$, R$_{2''}$ and R$_{2'''}$ are independently selected from the group consisting of hydrogen and (1C-4C)alkyl, wherein:
the alkyl group is optionally substituted with a moiety selected from the group consisting of —OH, —SH, —SeH, —C(O)OH, —NHC(NH)NH$_2$,

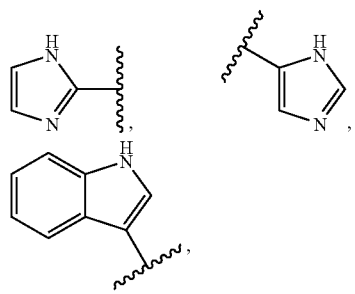

phenyl and

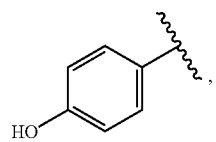

or
one or more of R$_2$, R$_{2'}$, R$_{2''}$ and R$_{2'''}$ may form a bridge between the carbon to which it is attached and the adjacent nitrogen, the bridge comprising —CH$_2$CH$_2$CH$_2$—;
R$_3$ and R$_{3'}$ are independently selected from the group consisting of (1C-12C)alkyl, (2C-12C)alkenyl, (3C-8C)cycloalkyl and —(CH$_2$CH$_2$O)$_q$CH$_2$CH$_2$—,
wherein q is an integer from 1 to 10, inclusive,
wherein the poly(ester-amide) is from about 0.05 mol % to about 5 mol % cross-linked.

In an aspect of this invention, M$_n$ is from about 20,000 Da to about 500,000 Da.

In an aspect of this invention, in the above implantable medical device, the crosslink is a chemical crosslink.

In an aspect of this invention, in the above implantable medical device, the chemical crosslink comprises a reaction product of an —OH, —SH, —NH$_2$ or —C(O)OH substituent on R$_2$, R$_{2'}$, R$_{2''}$, R$_{2'''}$ or R$_6$ with a multifunctional OH-reactive, —SH-reactive, —NH$_2$-reactive or —C(O)OH-reactive multifunctional crosslinking agent.

In an aspect of this invention, in the above implantable medical device, the OH-reactive, —SH-reactive, —NH$_2$-reactive or —C(O)OH-reactive multifunctional crosslinking agent comprises a diisocyanate.

In an aspect of this invention, in the above implantable medical device, the diisocyanate is selected from the group consisting of 1,2-ethanediisocyanate, 1,3-propanediisocyanate, 1,4-butanediisocyanate, 1,5-pentanediisocyanate, lysine diisocyanate and 1,4-cyclohexanediisocyanate.

In an aspect of this invention, in the above implantable medical device, R$_2$, R$_{2'}$, R$_{2''}$ and R$_{2'''}$ are independently selected from the group consisting of unsubstituted (1C-4C) alkyl and a bridge between the carbon to which it is attached and the adjacent nitrogen, the bridge comprising —CH$_2$CH$_2$CH$_2$—;
R$_5$ is selected from the group consisting of —CH(COR$_6$)CH$_2$S—, —CH(COR$_6$)CH$_2$O—, —CH(COR$_6$)(CH$_2$)$_4$NH—, —(CH$_2$)$_4$CH(COR$_6$)NH—, —CH(COR$_6$)CH(CH$_3$)O—,

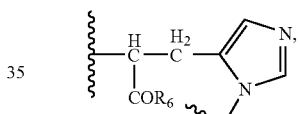

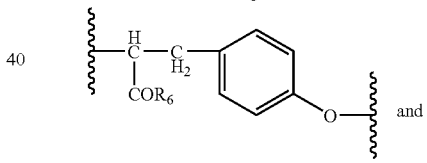

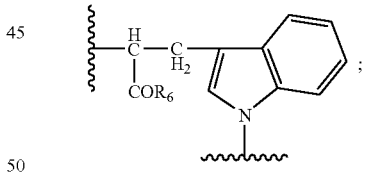

and,
R$_6$ is —OH.

In an aspect of this invention, in the above implantable medical device, R$_5$ is —(CH$_2$)$_4$CH(COR$_6$)NH—.

In an aspect of this invention, in the above implantable medical device, R$_2$ and R$_{2'}$ are —CH$_2$CH(CH$_3$)$_2$.

In an aspect of this invention, in the above implantable medical device, the OH-reactive, SH-reactive, NH$_2$ reactive, C(O)OH-reactive multifunctional crosslinking agent is a multifunctional aziridine compound.

In an aspect of this invention, in the above implantable medical device, the multifunctional aziridine compound is pentaerythriol tris(3-aziridinopropionate).

In an aspect of this invention, in the above implantable medical device, R$_2$, R$_{2'}$, R$_{2''}$ and R$_{2'''}$ are independently selected from the group consisting of unsubstituted (1C-4C)

alkyl and a bridge between the carbon to which it is attached and the adjacent nitrogen, the bridge comprising —$CH_2CH_2CH_2$—;

$R_5$ is selected from the group consisting of —$CH(COR_6)CH_2S$—, —$CH(COR_6)CH_2O$—, —$CH(COR_6)(CH_2)_4NH$—, —$(CH_2)_4CH(COR_6)NH$—, —$CH(COR_6)CH(CH_3)O$—,

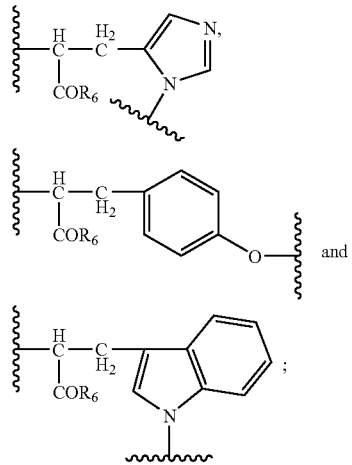

and,
$R_6$ is —OH.

In an aspect of this invention, in the above implantable medical device, $R_5$ is —$(CH_2)_4CH(COR_6)NH$—.

In an aspect of this invention, in the above implantable medical device, $R_2$ and $R_{2'}$ are —$CH_2CH(CH_3)_2$.

In an aspect of this invention, in the above implantable medical device, $R_1$ and $R_4$ are —$(CH_2)_8$ and $R_3$ is —$(CH_2)_6$—.

In an aspect of this invention, in the above implantable medical device, $R_5$ is selected from the group consisting of —$CH(COR_6)CH_2S$—, —$CH(COR_6)CH_2O$—, —$CH(COR_6)(CH_2)_4NH$—, —$(CH_2)_4CH(COR_6)NH$—, —$CH(COR_6)CH(CH_3)O$—,

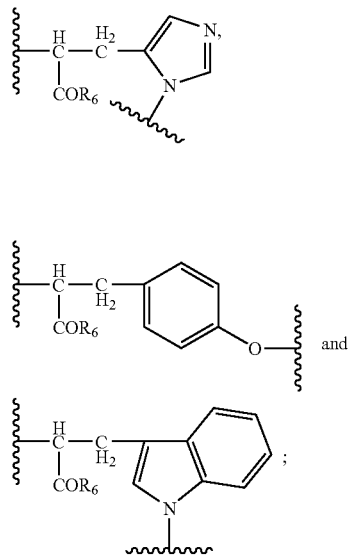

$R_6$ is selected from the group consisting of —$O(1C-20C)$alkenyl and —$O(CH_2CH_2O)_qCH_2CH_2OR_7$, wherein:
q is an integer from 0 to 600, inclusive;
$R_7$ is selected from the group consisting of —$C(O)CH=CH_2$ and —$C(O)C(CH_3)=CH_2$; and,
the chemical crosslink comprises UV or free-radical initiated reaction of the double bond.

In an aspect of this invention, in the above implantable medical device, in the aspect just above, $R_5$ is —$(CH_2)_4CH(COR_6)NH$—.

In an aspect of this invention, in the above implantable medical device, in the aspect just above, $R_6$ is selected from the group consisting of —$O(CH_2)_8CH=CH(CH_2)_7CH_3$ and

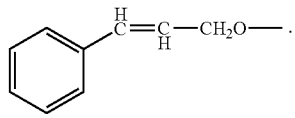

In an aspect of this invention, in the above implantable medical device, $R_1$ and $R_4$ are —$(CH_2)_8$—; $R_2$ and $R_{2'}$ are —$CH_2CH(CH_3)_2$ and $R_3$ is —$(CH_2)_6$.

In an aspect of this invention, in the above implantable medical device, $R_5$ is

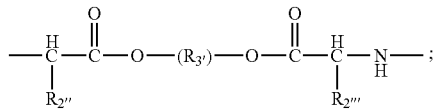

one of $R_1$ or $R_4$ is a (2C-12C)alkyenyl, the other is a (1C-12C)alkyl; or,
$R_1$ and $R_4$ are a (2C-12C)alkyenyl and the chemical crosslink comprises UV or free-radical initiated reaction of the alkenyl double bond.

In an aspect of this invention, in the above implantable medical device, n is 0; $R_1$ is a (2C-12C)alkenyl; and the chemical crosslink comprises UV or free-radical initiated reaction of the alkenyl double bond.

In an aspect of this invention, in the above implantable medical device, $R_2$ and $R_{2'}$ are —$(CH_2)CH(CH_3)_2$; and, $R_3$ is —$(CH_2)_6$—.

In an aspect of this invention, in the above implantable medical device, at least one of $R_2$, $R_{2'}$, $R_{2''}$, $R_{2'''}$ and $R_6$ comprises a —$C(O)OH$ group; and the chemical crosslink comprises an ionomer.

In an aspect of this invention, in the above implantable medical device, the ionomer comprises a monovalent cation.

In an aspect of this invention, in the above implantable medical device, the monovalent cation is selected from the group consisting of sodium, potassium, lithium and silver.

In an aspect of this invention, in the above implantable medical device, the ionomer comprises a polyvalent cation.

In an aspect of this invention, in the above implantable medical device, the polyvalent cation is selected from the group consisting of calcium(II), magnesium(II), zinc(II), iron(II) and aluminum(III).

In an aspect of this invention, in the above implantable medical device, $R_2$ and $R_{2'}$ are independently selected from the group consisting of hydrogen and (1C-4C)alkyl; $R_5$ is selected from the group consisting of —$CH(COR_6)CH_2S$—, —$CH(COR_6)CH_2O$—, —$CH(COR_6)(CH_2)_4NH$—, —$(CH_2)_4CH(COR_6)NH$—, —$CH(COR_6)CH(CH_3)O$—,

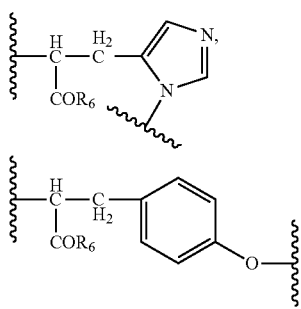

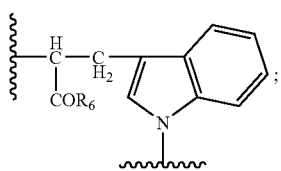

and

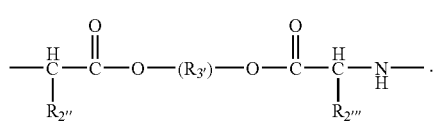

and $R_6$ is —OH.

In an aspect of this invention, in the above implantable medical device, in the aspect just above, $R_2$ and $R_{2'}$ are —$CH_2CH(CH_3)_2$; and $R_5$ is —$(CH_2)_4CH(COR_6)NH$—.

In an aspect of this invention, in the above implantable medical device, in the aspect just above, $R_1$ and $R_4$ are —$(CH_2)_8$—; $R_3$ is —$(CH_2)_6$—.

In an aspect of this invention, in the above implantable medical device, the ionomer herein comprises Zn(II).

In an aspect of this invention, in the above implantable medical device, the cross-link is a physical crosslink.

In an aspect of this invention, in the above implantable medical device, where the cross-link is physical, A is a soft segment; B is a hard segment; and, the physical crosslink comprises segregated domains of soft segments and paracrystalline hard segments.

In an aspect of this invention, in the above implantable medical device, A has a glass-transition temperature of 40° C. of lower; and, B has a glass transition temperature of 45° C. or higher.

In an aspect of this invention, in the above implantable medical device, $R_5$ is

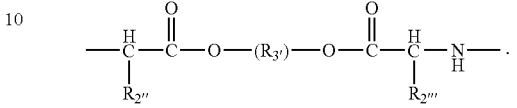

In an aspect of this invention, in the above implantable medical device, $R_1$ is —$(CH_2)_8$—; $R_2$ and $R_{2'}$ are —$(CH(CH_3)CH_2CH_3$; $R_3$ is —$(CH_2)_6$—; $R_{1'}$ is —$(CH_2)_4$—; $R_{2''}$ and $R_{2'''}$ are —$CH(CH_3)_2$ and $R_{3'}$ is —$(CH_2)_3$—.

In an aspect of this invention, in the above implantable medical device, $R_1$ is —$(CH_2)_4$—; $R_2$ and $R_2$ are —$(CH(CH_3)CH_2CH_3$; $R_3$ is —$(CH_2)_{12}$—; $R_{1'}$ is —$(CH_2)_4$—; $R_{2''}$ and $R_{2'''}$ are —$CH(CH_3)_2$ and $R_{3'}$ is —$(CH_2)_3$—.

In an aspect of this invention, in the above implantable medical device, $R_1$ is —$(CH_2)_8$—; $R_2$, $R_{2'}$, $R_{2''}$ and $R_{2'''}$ are —$CH(CH_3)CH_2CH_3$; $R_3$ is —$(CH_2)_6$—; $R_{1'}$ is —$(CH_2)_2$— and $R_{3'}$ is —$(CH_2)_2$—.

In an aspect of this invention, in the above implantable medical device, A is amorphous; B is crystalline; and the crosslink comprises inter-chain crystallization.

In an aspect of this invention, in the above implantable medical device, where A is amorphous and B is crystalline, $R_5$ is

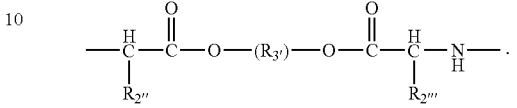

In an aspect of this invention, in the above implantable medical device, where A is amorphous and B us crystalline, $R_1$ is —$(CH_2)_8$—; $R_{1'}$ is —$(CH_2)_4$—; $R_2$ and $R_{2'}$ are —$CH_2CH(CH_3)_2$; $R_{2''}$ and $R_{2'''}$ are $CH_2$ phenyl; $R_3$ is —$(CH_2)_6$—; and, $R_{3'}$ is —$(CH_2)_4$—.

In an aspect of this invention, in the above implantable medical device, at least the drug reservoir layer comprises a crosslinked poly(ester-amide) of this invention.

In an aspect of this invention, in the above implantable medical device, at least the rate-controlling layer comprises a crosslinked poly(ester-amide) of this invention.

In an aspect of this invention, in the above implantable medical device, at least the topcoat layer comprises a crosslinked poly(ester-amide) of this invention.

In an aspect of this invention, in the above implantable medical device, the implantable medical device is a stent.

DETAILED DESCRIPTION

Use of the singular herein includes the plural and visa versa unless expressly stated to be otherwise. That is, "a" and "the" refer to one or more of whatever the word modifies. For example, "a therapeutic agent" includes one such agent, two such agents, etc. Likewise, "the layer" may refer to one, two or more layers and "the polymer" may mean one polymer or a plurality of polymers. By the same token, words such as, without limitation, "layers" and "polymers" would refer to one layer or polymer as well as to a plurality of layers or polymers unless, again, it is expressly stated or obvious from the context that such is not intended.

As used herein, any words of approximation such as without limitation, "about," "essentially," "substantially" and the like mean that the element so modified need not be exactly what is described but can vary from the description by as much as ±15% without exceeding the scope of this invention.

As used herein, a poly(ester-amide) refers to a polymer that has in its backbone structure both ester and amide bonds. The poly(ester-amides) of this invention have the generic formula:

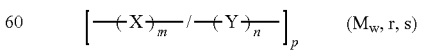 (M$_w$, r, s)

wherein X and Y are the constitutional units of the polymer.

As used herein, the term "constitutional unit" refers to the repeating units that make up the polymer. For example, in the following poly(ester-amide) of this invention:

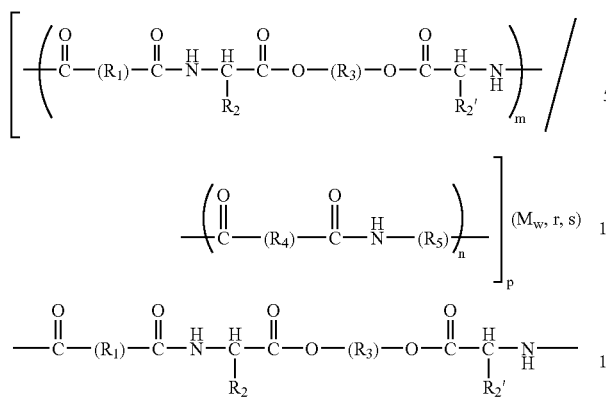

is the X constitutional unit and

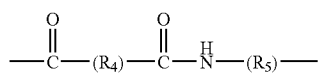

is the Y constitutional unit. The constitution units on the other hand may themselves be comprised of the reaction product of other compounds. For example, without limitation, the X constitutional unit above can result from the reaction of an amino acid,

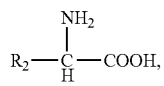

with a diol, HO—($R_3$)—OH, to give a diamino ester,

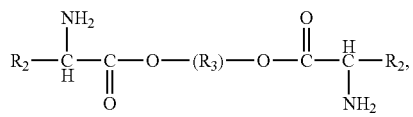

which is then reacted with a diacid,

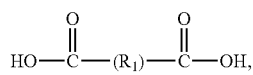

to give the constitutional unit. The amine group, the carboxylic acid group or the hydroxyl group may be "activated," i.e., rendered more chemically reactive, to facilitate the reactions if desired; such activating techniques are well-known in the art and the use of any such techniques is within the scope of this invention. A non-limiting example of the synthesis of an exemplary but not limiting X constitution unit having the above general structure is the reaction of 1,6-hexane diol with 1-leucine to give the diamino diester, which is then reacted with sebacic acid to give X. Constitutional unit Y can be obtained by the same reactions as those affording X but using one or more different reactants such that the resulting constitutional units X and Y are chemically different or Y may result from the reaction of a diacid with a tri-functional amino acid wherein two of the functional groups are capable of reacting with the diacid. As example of the foregoing would be the reaction of sebacic acid or an activated derivative thereof, with 1-lysine, i.e., 2,6-diaminohexanoic acid.

With regard to the synthesis of the poly(ester-amide)s of this invention, it will be noted that no specific reactions or reaction conditions are exemplified herein. This is because the reactions and reaction conditions both for the preparation of constitutional units and for the preparation of the final poly(ester-amide) are standard organic and organic polymer chemistry well-known to those of ordinary skill in the art and, therefore, those skilled artisan would be able to prepare any of the compounds herein without undue experimentation based on the disclosures herein.

As for the amino acids selected for the preparation of poly(ester-amide)s of this invention, any may be use; however, at present it is preferred that the amino acids be selected from the group commonly known as the standard amino acids or sometimes the proteinogenic amino acids because they are encoded by the normal genetic code. There currently are 20 standard amino acids: alanine, arginine, asparagine, aspartic acid, cysteine, glutamic acid, glutamine, glycine, histidine, isoleucine, leucine, lysine, methionine, phenyl alanine, proline, serine, threonine, tryptophan, tyrosine and valine. Relatively recently selenoadenine has been found to be incorporated into a number of proteins and is included with the above as a particularly useful amino acid of this invention. In naturally-occurring biological proteins, these amino acids appear as the l-enantiomeric isomers but for the purposes of this invention they may be used as their l- or d-enantiomers or as racemic mixtures.

In the above formula, m and n are integers that represent the average number of constitutional units X and Y in an uninterrupted string, i.e., the number of X units before a Y unit is encountered, etc. The integers m and n can be any number, including 0, in which case the resulting poly(ester-amide) would be a homopolymer.

In the above formula, p represents the total number of X and Y units in the polymer and can be any integer from 1 to about 2500, with the proviso that the combination of m, n and p should provide a poly(ester-amide) that has a molecular weight within the range discussed below.

In the above formula, $M_n$ represents the number average molecular weight of a poly(ester-amide) of this invention. Again, while any molecular weight that results in a polymer that has the requisite properties to be disposed as a layer over an implantable medical device of this invention is within the scope of this invention, at present the number average molecular weight of a poly(ester-amide) of this invention is from about 10,000 Da (Daltons) to about 1,000,000 Da, preferably at present from about 20,000 Da to about 500,000 Da.

Also in the above formula, s and t represent the mole fraction of each of the constitutional units. Each of s and t is a number between 0 and 1, inclusive with s+t=1. The mole fraction and the number of constitutional units are obviously related and it is understood that the designation of one will affect the other.

As noted s and t may each be 0, 1 or any fraction between. The only proviso is that m can be 0 only if $R_5$ is selected from the group consisting of —CH(COR$_6$)CH$_2$S—, —CH(C(O)R$_6$CH$_2$O—, —CH(COR$_6$)CH(CH$_3$)O— and

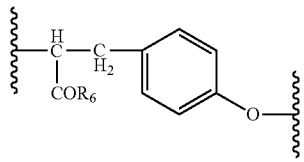

because otherwise the resulting homopolymer would not be a poly(ester-amide). Other than the foregoing proviso, m and n can be any number in the given range and those skilled in the art will be able, based on the disclosures herein, vary m and n to impart on the final polymer any type of desired property that varying the mole fractions can achieve depending on which type of layer, as set forth herein, is being contemplated.

The polymers of this invention may be regular alternating polymers, random alternating polymers, regular block polymers, random block polymers or purely random polymers unless expressly stated to be otherwise. A regular alternating polymer has the general structure: . . . x-y-z-x-y-z-x-y-z- . . . . A random alternating polymer has the general structure: . . . x-y-x-z-x-y-z-y-z-x-y- . . . , it being understood that the exact juxtaposition of the various constitution units may vary. A regular block polymer has the general structure: . . . x-x-x-y-y-y-z-z-z-x-x-x . . . , while a random block polymer has the general structure: . . . x-x-x-z-z-x-x-y-y-y-y-z-z-z-x-x-z-z-z- . . . . Similarly to regular and alternating polymers, the juxtaposition of blocks, the number of constitutional units in each block and the number of blocks in a particular block polymer of this invention are not in any manner limited by the preceding illustrative generic structures.

As used herein, "alkyl" refers to a straight or branched chain fully saturated (no double or triple bonds) hydrocarbon (carbon and hydrogen only) group. Examples of alkyl groups include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, and cyclohexyl. As used herein, "alkyl" includes "alkylene" groups, which refer to straight or branched fully saturated hydrocarbon groups having two rather than one open valences for bonding to other groups. Examples of alkylene groups include, but are not limited to methylene, —CH$_2$—, ethylene, —CH$_2$CH$_2$—, propylene, —CH$_2$CH$_2$CH$_2$—, n-butylene, —CH$_2$CH$_2$CH$_2$CH$_2$—, sec-butylene, —CH$_2$CH$_2$CH(CH$_3$)— and the like.

As used herein, "mC to nC," wherein m and n are integers refers to the number of possible carbon atoms in the indicated group. That is, the group can contain from "m" to "n", inclusive, carbon atoms. An alkyl group of this invention may comprise from 1 to 12 carbon atoms, that is, m is 1 and n is 12. Of course, a particular alkyl group may be more limited. For instance without limitation, an alkyl group of this invention may consist of 3 to 8 carbon atoms, in which case it would be designated as a (3C-8C)alkyl group. The numbers are inclusive and incorporate all straight or branched chain structures having the indicated number of carbon atoms. For example without limitation, a "C$_1$ to C$_4$ alkyl" group refers to all alkyl groups having from 1 to 4 carbons, that is, CH$_3$—, CH$_3$CH$_2$—, CH$_3$CH$_2$CH$_2$—, CH$_3$CH(CH$_3$)—, CH$_3$CH$_2$CH$_2$CH$_2$—, CH$_3$CH$_2$CH(CH$_3$)— and (CH$_3$)$_3$CH—.

As use herein, a cycloalkyl group refers to an alkyl group in which the end carbon atoms of the alkyl chain are covalently bonded to one another. The numbers "m" and "n" refer to the number of carbon atoms in the ring formed. Thus for instance, a (3C-8C)cycloalkyl group refers to a three, four, five, six, seven or eight member ring, that is, cyclopropane, cyclobutane, cyclopentane, cyclohexane, cycloheptane and cyclooctane.

As used herein, "alkenyl" refers to an alkyl group that contains in the straight or branched hydrocarbon chain one or more double bonds.

Standard shorthand designations well-known to those skilled in the art are used throughout this application. Thus the intended structure will easily be recognizable to those skilled in the art based on the required valence of any particular atom with the understanding that all necessary hydrogen atoms are provided. For example, —COR or —C(O)R, because carbon is tetravalent, must refer to the structure

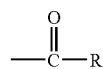

as that is the only way the carbon can be tetravalent without the addition of hydrogen or other atoms no shown in the structure. Likewise, it is understood by those skilled in the chemical arts that so-called stick structure, exemplified by

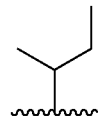

represents the structure

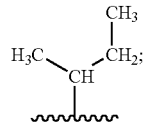

that is, each terminus is capped with a CH$_3$ group and the apex of each angle is a carbon atom with the requisite number of hydrogens attached.

As used herein, a "crosslink" refers to a small region in a macromolecule involving at least two discrete polymer chains and from which at least 4 chains emanate. Crosslinking results in the motion of the individual chains involved to be restricted with respect to other chains involved in the crosslink. For purposes of this invention, a crosslink may comprise covalent or ionic links between the chains, which is referred to herein as a "chemical crosslink" or it may be the result of non-bonded interactions of regions of the individual chains, which are referred to herein as "physical crosslinks."

Covalent bond chemical crosslinks are created using chemical reactions well-known to those of ordinary skill in organic chemistry. For the purposes of this invention, covalent chemical crosslinks are of two types. The first type involves the reaction of a functional group appended to a polymer backbone with a multifunctional crosslinking agent. As used herein, a "multifunctional crosslinking agent" is a compound having two or more functional groups that are capable of reacting with a functional group appended to the polymer backbone. As a non-limiting example, the functional group appended to the polymer backbone can be a hydroxyl, —OH, group and the multifunctional crosslinking agent can be a diisocyanate. The cross-linking reaction is shown schematically in Scheme 1:

Scheme 1

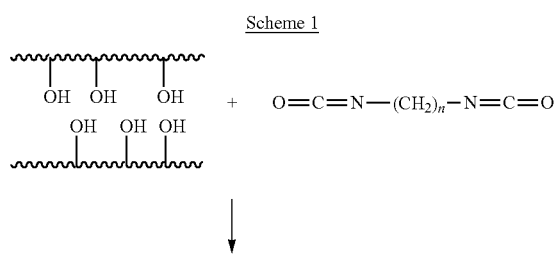

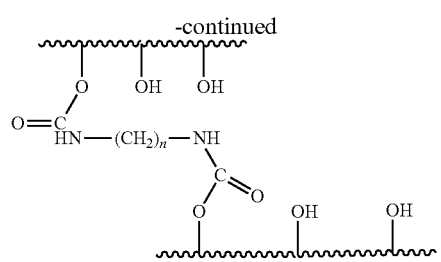

where the wavy line represents the polymer backbone and the crosslink comprises carbamate, —OC(O)NH—, groups. Of course, depending on how much diisocyanate is used, more than one hydroxyl group per polymer chain may become involved in crosslink formation.

If the hydroxyl group is replaced with a mercapto, —SH, group, the crosslink comprises a thiocarbamate, —SC(O)NH—.

If the hydroxyl is replaced by an amino, —NH$_2$, group, the crosslink comprises a urea, —NHC(O)NH—.

If the hydroxyl is replaced by a carboxyl, —C(O)OH, group, the crosslink comprises an amide, —C(O)NH—, group. A non-limiting example of a chemically crosslinked segment of a poly(ester-amide) of this invention involving the reaction of an isocyanate and a carboxyl group is the following:

Scheme 2

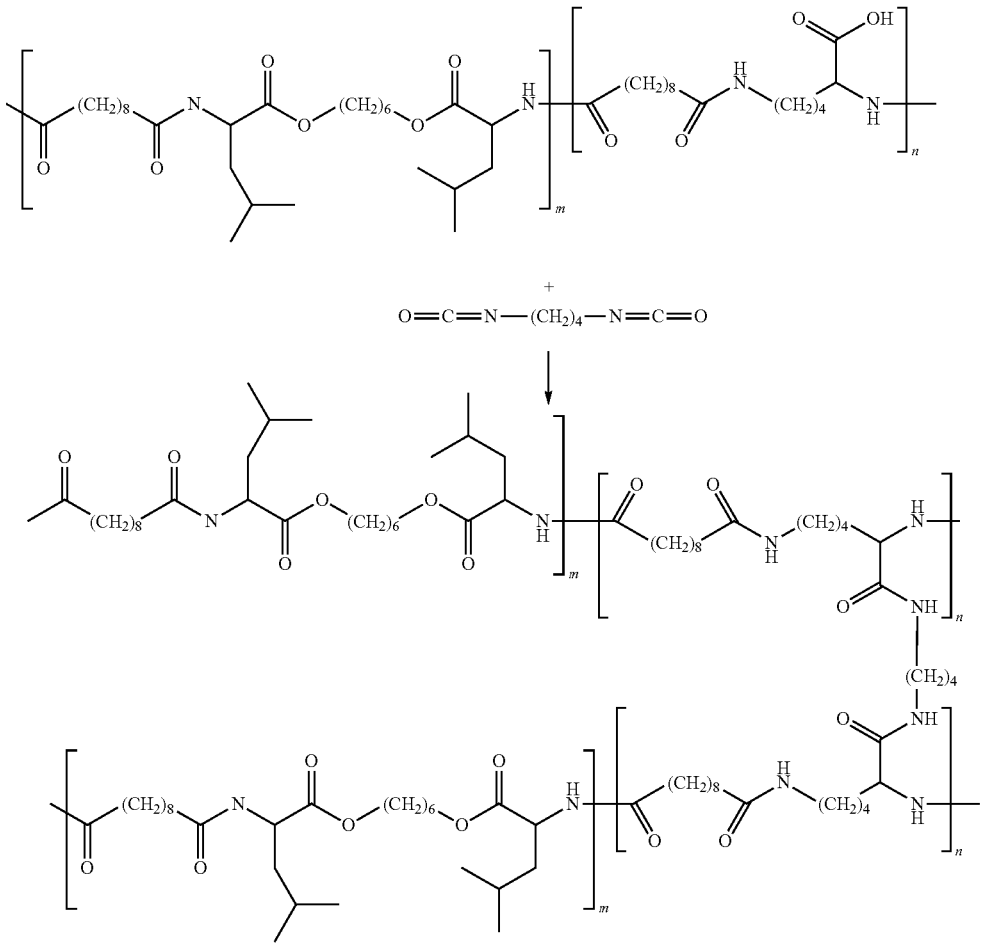

For the sake of clarity and simplicity only a segment of a poly(ester-amide) and one crosslink is shown in the above scheme (and all other schemes herein). It is understood that in actuality two polymer chains may have a one or a plurality of crosslinks between them and one polymer chain may be crosslinked to a plurality of other polymer chains.

Another multifunctional chemical crosslinking agent is pentaerythritol tris(3-aziridinopropionate). Aziridines are known to react with active $H^+$ functional groups such as carboxyls as exemplified by the following non-limiting example (Scheme 3):

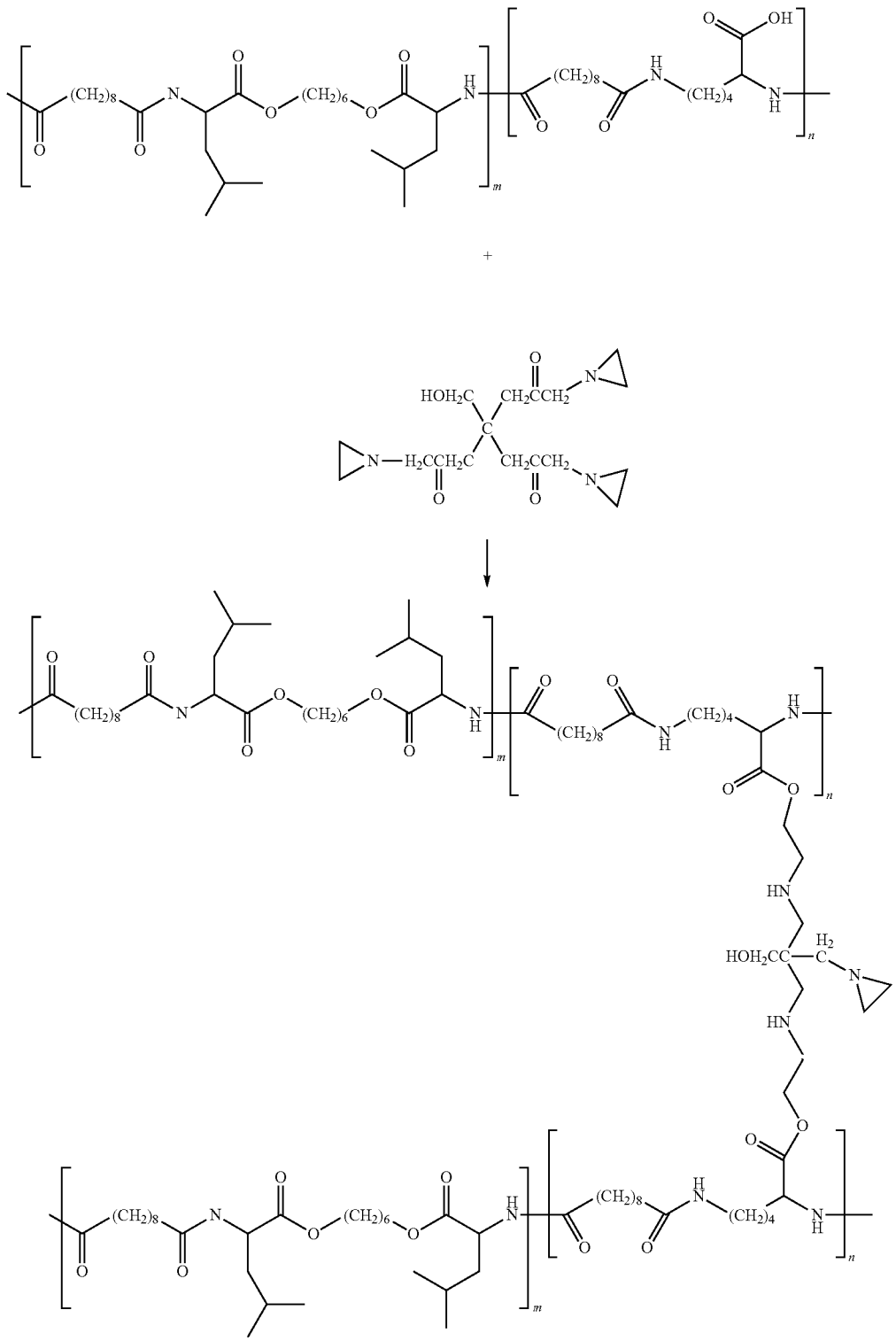

Scheme 3

The remaining aziridine group in the above product may, of course, also react with a polymer chain to give a three-way crosslink.

Many other chemical crosslinking agents that can react with —OH, —SH, —NH$_2$ and —C(O)OH groups are known to those skilled in the art and the use of any of them to crosslink poly(ester-amide)s is within the scope of this invention.

The second type of chemical crosslink for the purposes of this invention is the UV light- or free radical-initiated reaction of two double bonds, referred to herein as ethylenic groups and having the chemical structure —CR═CR—, wherein R may be hydrogen or a lower alkyl but at present is preferably hydrogen. This well-established reaction results in the formation of a single covalent bond between a carbon of one ethylenic group and a carbon of another ethylenic group. The ethylenic groups may be incorporated into the backbone of the polymer (Scheme 4):

Scheme 4

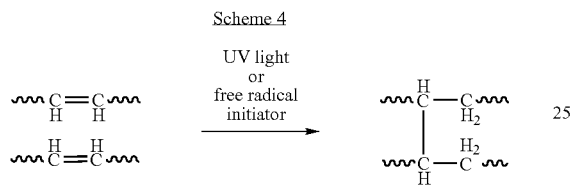

Scheme 5 shows a non-limiting example of a UV or free radical initiated crosslinked segment of a poly(ester-amide) of this invention:

Scheme 5

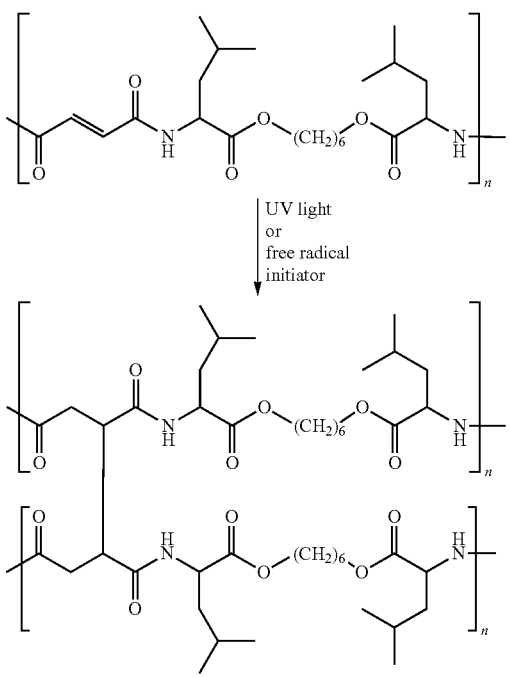

In the alternative, the ethylenic group may be incorporated in a group appended to the polymer backbone as shown in the following non-limiting example of yet another crosslinked poly(ester-amide) segment of this invention (Scheme 6):

Scheme 6

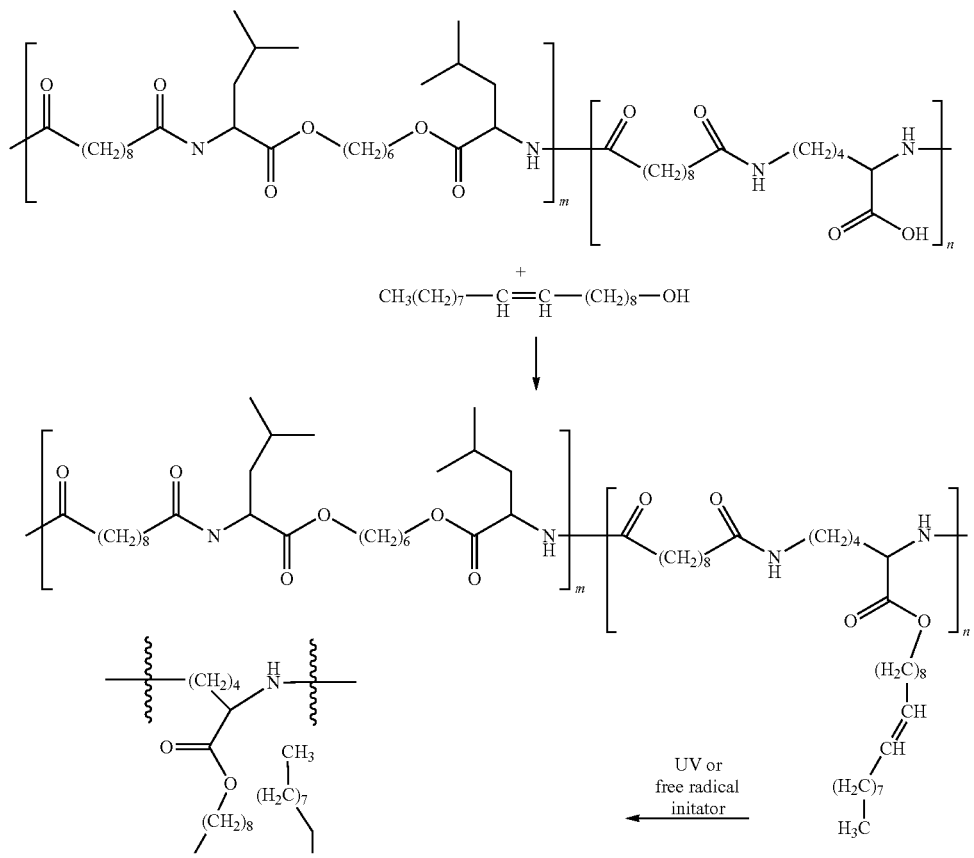

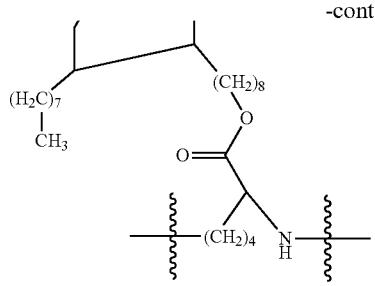

It is also possible to achieve UV- or free radical-initiated crosslinks using a crosslinking reagent that itself has ethylenic groups. An example, without limitation, of such a crosslinking agent is poly(ethylene glycol) bismethacrylate, $CH_2=C(CH_3)C(O)O(CH_2CH_2O)_nCH_2CH_2OC(O)C(CH_3)=CH_2$ (MA-PEG-MA). When used to crosslink a poly(ester-amide) of this invention, one of the MA-PEG-MA ethylenic groups reacts with an ethylenic groups of one polymer chain and the other ethylenic group of the MA-PEG-MA reacts with an ethylenic group of a different chain.

The other type of chemical crosslink for the purposes of this invention is the formation of ionic bonds between metal cations ($M^{+}$) and carboxyl anions, $-C(O)O^{-}$, appended to the backbone of a poly(ester-amide) herein. Polymers crosslinked in this manner are referred to as ionomers. Ionomers "cross-link" polymers by two mechanisms, although there is a great deal of overlap. The first mechanism occurs when a carboxylic acid, $-C(O)OH$, group appended to a polymer backbone is reacted with a divalent base, for example without limitation, $Zn(OH)_2$. The $Zn(II)$ reacts with carboxyl groups of two different polymer chains, binding them together with the ionic bonds formed and thereby "crosslinking" the polymer chains. A non-limiting example of a divalent cation crosslinked segment of a poly(ester-amide) of this invention is shown in Scheme 7:

Scheme 7

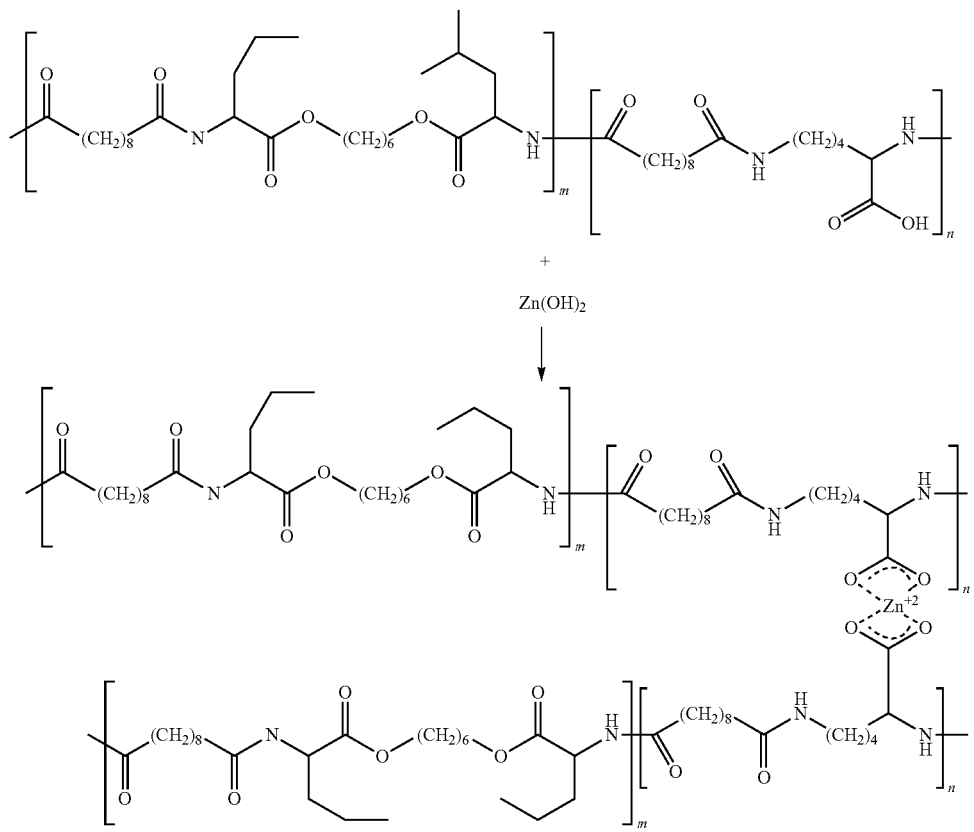

If, on the other hand, a monovalent cation is used, such as, without limitation, $Na^{+}$, it is capable of reacting with only one carboxyl group. The ionic group formed, i.e., $Na^{+}\ ^{-}OC(O)$-polymer, however, tend to come together with other such group on other polymer chains, in effect causing many polymer chains to cluster together via their ionic groups. The ionic forces holding the clusters together impede the motion of the involved polymer chains just as a covalent bind crosslink does. Thus, the formation of ionic clusters in effect "crosslinks" the polymer chains. Without being held to any particular theory, it is believed that the clustering of ionic groups results from the phase separation of the fundamentally hydrophobic polymer backbone and the hydrophilic ionic groups. Ionomers, however, are not formally crosslinked, which requires the formation of covalent bonds between polymer chains. Thus, the ionic clusters of ionomers can be relatively easily be disrupted by forces such as heating, which increases the both the degree and vigor of molecular motion in the polymer chains to the point that the clusters are dispersed. Despite this sensitivity to external forces, when used under their designated operating conditions, the clusters are primarily responsible for the physical properties of ionomers, which physical properties can, in some instances, be quite remarkable. For instance, without limitation, ionomers can be extremely tough, so much so that they are often used to make products requiring great resiliency as the outer covering on golf balls.

While the chemically crosslinked polymers of this invention can be of any type: homopolymers, alternating polymers, random alternating polymers, alternating block polymers, random block polymers or completely random polymers, physically crosslinked polymers of this invention must be block copolymers.

The first kind of physically cross-linked poly(ester-amide) of this invention involves multi-block copolymers consisting of alternating hard and soft segments. Hard segments and soft segments are differentiated primarily by their glass transition temperatures, $T_g$. ($T_g$) is the temperature at which a polymer (or a segment of a polymer) changes mechanical properties from those of a rubber (i.e., elastic) to those of a glass (brittle). Below the $T_g$ the polymeric molecules have very little translational freedom, i.e., they are unable to move easily or very far in relation to one another. Rather than moving around to adapt to an applied stress, they tend to separate violently so that the polymer breaks or shatters similarly to a pane of glass that is stressed. Above $T_g$, relatively facile segmental motion becomes possible and the polymer chains are able to move around and slip by one another such that when a stress is applied to the polymer it bends and flexes rather than breaks.

For the purpose of this invention, the $T_g$ of the soft segment must be at or below the temperature of the intended operating environment, which is the body of a living mammal. While the normal body temperature of mammals differs considerably, the primary mammal to which this invention is presently intended to apply is humans, which have a normal body temperature of approximately 37° C. Thus, it is presently preferred that the soft segment of poly(ester-amides) of this invention have a $T_g$ at or below about 37° C. such that, when placed in a human body, the soft segments will, when they equilibrate to body temperature, be in an elastic rather than glass-like mode.

Of course, the poly(ester-amide)s of this invention may be used with other mammals having quite different normal body temperatures from humans; those skilled in the art will be able to determine what the proper $T_g$s should be for particular mammals based on the disclosure herein and all such poly (ester-amides) for use with any mammal are within the scope of this invention.

Conversely, the hard segments of the poly(ester-amides) of this invention must be in a brittle glass-like rather than elastic mode when subjected to mammalian body temperature in order to create in their working environment the soft segment/hard segment morphology necessary to engage in this manner of crosslinking. To accomplish this, the hard segments have a $T_g$ that is above 37° C. and, of course, above the $T_g$ of the soft segments. It is presently preferred that the hard segments of the poly(ester-amides) of this invention have a $T_g$ that is at least 5° C., preferably at least 15° C. and most preferably at present at least 25° C. above the body temperature of the projected patients in whom the polymers are to be used.

In general, for this type of physical crosslinking, it is presently preferred that the degree of polymerization within the hard and soft segments is such that n and m are both greater than or equal to about 10. Further, while there is no absolute upper limit, it is presently preferred that the hard and soft segments have a degree of polymerization from about 10 to about 100. The block copolymer comprised of the foregoing hard and soft segments will preferably at present have a degree of polymerization at least an order of magnitude greater than the degree of polymerization within the segments.

When subject to a temperature of about 37° C. or higher (but below the $T_g$ of the hard segment), a poly(ester-amide) of this invention that meets the above criteria will phase separate into a soft-segment phase and a hard-segment phase due to chemical and physical incompatibility of the segments. The soft segments will remain in a random array of polymer chains and will retain their elastic properties. The hard segments, on the other hand, due to their rigid structure, will tend to align with one another, that is, hard segments of different polymer chains will come together into what can be described as a paracrystalline structure. Paracrystalline simply means that the aligned segments display some short range order when examined by x-ray diffraction but they do not exhibit the intricate long range order of true crystals. The aligned hard segments, held together by physical forces such as hydrogen bonding, van der Waals forces and the like, resist separation and act as multifunctional spacious crosslinked regions. It should be noted that the hard segments need not have any crystallinity whatsoever. Their $T_g$s, which are above the operating temperature, together with the fact that they will phase separate into particular domains alone permits them to act as physical crosslinkers.

Non-limiting examples of soft segment/hard segment poly (ester-amides) of this invention, together with the $T_g$s of the segments are:

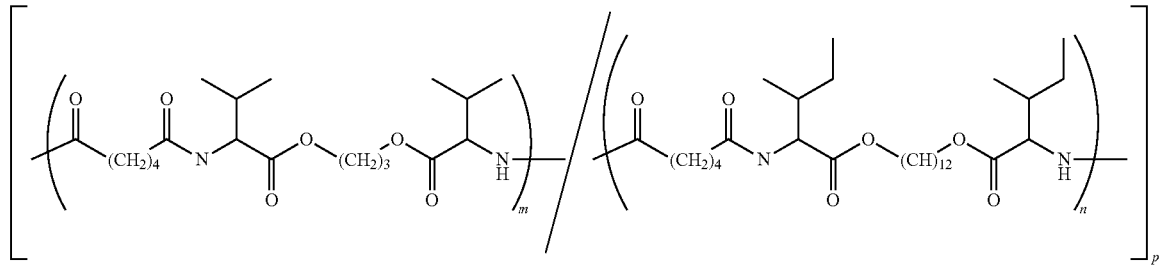

and

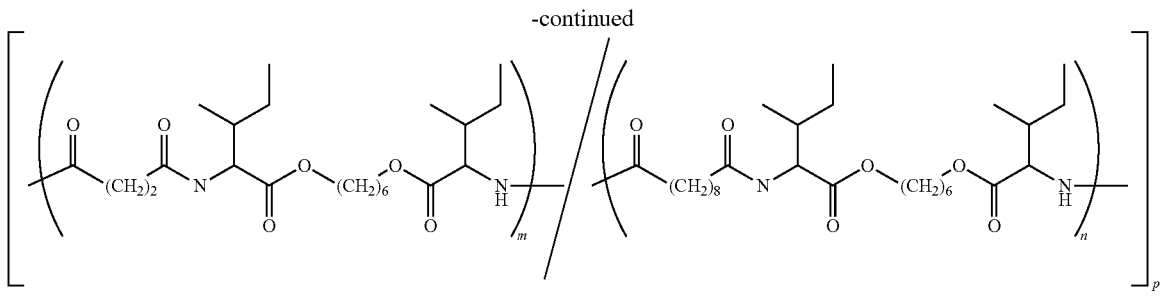

$T_g > 45°$ C.  $T_g = 28°$ C.

Based on the disclosures herein, numerous additional soft segment/hard segment poly(ester-amide)s having the requisite chemical and physical properties to be useful for the purposes of this invention, will become apparent to those skilled in the art and all such compounds are within the scope of this invention.

A further type of physically crosslinked poly(ester-amide) of this invention comprises a unique subset of the preceding soft segment/hard segment polymer, namely, wherein the hard segment is crystalline.

When a segment of a polymer exhibits sufficient structural regularity, those regions of separate chains may come together in an aligned configuration and ultimately form crystalline structures. Polymer crystallization is believed to follow the classical growth pattern of crystalline small molecules. That is, crystallization begins with nucleation, the formation of small crystalline particles around a bit of debris in the sea of liquid polymer. These nuclei grow in a hierarchy of ordered structures, namely into lamellae and, eventually, into crystallites. Unlike the paracrystalline soft segment/hard segment structures discussed previously herein, the crystalline regions of polymers exhibit considerable long-range order when subjected to x-ray diffraction examination. Also unlike soft segment/hard segment paracrystalline crosslinks, crystalline regions of polymers are substantially more robust and will maintain in a crosslinked configuration until the melting point, $T_m$, which is a determinable number, of the crystalline regions is reached at which time the crystal structures "melt" similarly to small molecules crystals and become amorphous.

A non-limiting example of a crystalline poly(ester-amide) of this invention is shown below:

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves and cerebrospinal fluid shunts. An implantable medical device specifically designed and intended solely for the localized delivery of a therapeutic agent is within the scope of this invention.

As used herein, "device body" refers to an implantable medical in a fully formed utilitarian state with an outer surface to which no coating or layer of material different from that of which the device is manufactured has been applied. By "outer surface" is meant any surface however spatially oriented that is in contact with bodily tissue or fluids. A common example of a "device body" is a BMS, i.e., a bare metal stent, which, as the name implies, is a fully-formed usable stent that has not been coated with a layer of any material different from the metal of which it is made on any surface that is in contact with bodily tissue or fluids. Of course, device body refers not only to BMSs but to any uncoated device regardless of what it is made of.

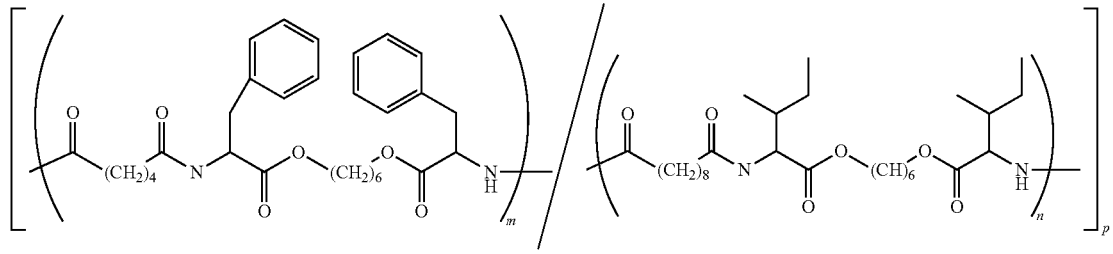

$T_m = 104°$ C., $T_g = 59°$ C.  $T_g = 28°$ C.

Those skilled in the art will be able, based on the disclosures herein, to envision numerous additional soft segment/crystalline segment poly(ester-amides); all are within the scope of this invention.

Implantable medical devices made of virtually any material, i.e., materials presently known to be useful for the manufacture of implantable medical devices and materials that may be found to be so in the future, may be used with a coating of this invention. For example, without limitation, an implantable medical device useful with this invention may be made of one or more biocompatible metals or alloys thereof including, but not limited to, cobalt-chromium alloy (ELGILOY, L-605), cobalt-nickel alloy (MP-35N), 316L stainless steel, high nitrogen stainless steel, e.g., BIODUR 108, nickel-titanium alloy (NITINOL), tantalum, platinum, platinum-iridium alloy, gold and combinations thereof.

Implantable medical devices may also be made of polymers that are biocompatible and biostable or biodegradable, the latter term including bioabsorbable and/or bioerodable.

As used herein, "biocompatible" refers to a polymer that both in its intact, that is, as synthesized, state and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

Among useful biocompatible, relatively biostable polymers are, without limitation polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Biocompatible, biodegradable polymers include naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

One or more synthetic or semi-synthetic biocompatible, biodegradable polymers may also be used to fabricate an implantable medical device useful with this invention. As used herein, a synthetic polymer refers to one that is created wholly in the laboratory while a semi-synthetic polymer refers to a naturally-occurring polymer than has been chemically modified in the laboratory. Examples of synthetic polymers include, without limitation, polyphosphazines, polyphosphoesters, polyphosphoester urethane, polyhydroxyacids, polyhydroxyalkanoates, polyanhydrides, polyesters, polyorthoesters, polycarbonates, polyiminocarbonates, polyamino acids, polyoxymethylenes, poly(esteramides) and polyimides.

Blends and copolymers of the above polymers may also be used and are within the scope of this invention. Based on the disclosures herein, those skilled in the art will recognize those implantable medical devices and those materials from which they may be fabricated that will be useful with the coatings of this invention. At present, preferred implantable medical devices for use with the coatings of this invention are stents.

A stent refers generally to any device used to hold tissue in place in a patient's body. Particularly useful stents, however, are those used for the maintenance of the patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an artery thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, neuro, carotid, coronary, pulmonary, aorta, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. In fact, therapeutic agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. In any event, due to the expansion of the stent, any coating thereon must be flexible and capable of elongation.

As use herein, a material that is described as a layer "disposed over" an indicated substrate, e.g., without limitation, a device body or another layer, refers to a relatively thin coating of the material applied, preferably at present, directly to essentially the entire exposed surface of the indicated substrate. By "exposed surface" is meant that surface of the substrate that, in use, would be in contact with bodily tissues or fluids. "Disposed over" may, however, also refer to the application of the thin layer of material to an intervening layer that has been applied to the substrate, wherein the material is applied in such a manner that, were the intervening layer not present, the material would cover substantially the entire exposed surface of the substrate. As used herein, a "primer layer" refers to a coating consisting of a polymer or blend of polymers that exhibit good adhesion characteristics with regard to the material of which the device body is manufactured and good adhesion characteristic with regard to whatever material is to be coated on the device body. Thus, a primer layer serves as an adhesive intermediary layer between a device body and materials to be carried by the device body and is, therefore, applied directly to the device body. Examples, without limitation, of primers include silanes, titanates, zirconates, silicates, parylene, polyacrylates and polymethacrylates, with poly(n-butyl methacrylate) being a presently preferred primer.

As used herein, "drug reservoir layer" refers either to a layer of one or more therapeutic agents applied neat or to a layer of polymer or blend of polymers that has dispersed within its three-dimensional structure one or more therapeutic agents. A polymeric drug reservoir layer is designed such that, by one mechanism or another, e.g., without limitation, by elution or as the result of biodegradation of the polymer, the therapeutic substance is released from the layer into the surrounding environment.

As used herein, "therapeutic agent" refers to any substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

As used herein, the terms "drug" and "therapeutic agent" are used interchangeably.

As used herein, "rate-controlling layer" refers to a polymeric layer that is applied over a drug reservoir layer to modify the rate of release into the environment of the therapeutic agents from the drug reservoir layer. A rate-controlling layer may be used simply to "tune" the rate of release of a therapeutic agent to exactly that desired by the practitioner or it may be a necessary adjunct to the construct because the polymer or blend of polymers with which the therapeutic agent is compatible with regard to coating as a drug reservoir layer may be too permeable to the therapeutic substance resulting in too rapid release and delivery of the therapeutic substance into a patient's body. In such case, a layer may be placed between the drug reservoir layer and the external environment wherein the layer comprises a polymer that, due to its inherent properties or because it has been cross-linked, presents a more difficult to traverse barrier to an eluting drug. The rate-controlling propensity of this layer will depend, without limitation, on such factors as the amount of this polymer in the layer, the thickness of the layer and the degree of cross-linking of the polymer.

As used herein, a "topcoat layer" refers to an outermost layer, that is, a layer that is in contact with the external environment and that is coated over all other layers. The topcoat layer may be applied to provide better hydrophilicity to the device, to better lubricate the device or merely as a device protectant. The topcoat layer, however, may also contain therapeutic agents, in particular if the treatment protocol being employed calls for essentially immediate release of one or more therapeutic agent (these being included in the topcoat layer) followed by the controlled release of another therapeutic agent or agents over a longer period of time. In addition, the topcoat layer may contain one or more "biobeneficial agents."

A "biobeneficial" agent is one that beneficially affects an implantable medical device by, for example, reducing the tendency of the device to protein foul, increasing the hemocompatibility of the device, and/or enhancing the non-thrombogenic, non-inflammatory, non-cytotoxic, non-hemolytic, etc. characteristics of the device. Some representative biobeneficial materials include, but are not limited to, polyethers such as poly(ethylene glycol) (PEG) and poly(propylene glycol); copoly(ether-esters) such as poly(ethylene oxide-co-lactic acid); polyalkylene oxides such as poly(ethylene oxide) and poly(propylene oxide); polyphosphazenes, phosphoryl choline, choline, polymers and copolymers of hydroxyl bearing monomers such as hydroxyethyl methacrylate, hydroxypropyl methacrylate, hydroxypropylmethacrylamide, poly (ethylene glycol) acrylate, 2-methacryloyloxyethylphosphorylcholine (MPC) and n-vinyl pyrrolidone (VP); carboxylic acid bearing monomers such as methacrylic acid, acrylic acid, alkoxymethacrylate, alkoxyacrylate, and 3-trimethylsilylpropyl methacrylate; polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functionalized poly(vinyl pyrrolidone); biomolecules such as fibrin, fibrinogen, cellulose, starch, collagen, dextran, dextrin, hyaluronic acid, heparin, glycosamino glycan, polysaccharides, elastin, chitosan, alginate, silicones, PolyActive™, and combinations thereof. PolyActive™ refers to a block copolymer of poly(ethylene glycol) and poly(butylene terephthalate).

An implantable medical device of this invention may include one or more therapeutic agents. Virtually any therapeutic agent found to be useful when incorporated on and implantable medical device may be used in the device and method of this invention. Examples of therapeutic agents include, but are not limited to anti-proliferative, anti-inflammatory, antineoplastic, antiplatelet, anti-coagulant, anti-fibrin, antithrombonic, antimitotic, antibiotic, antiallergic and antioxidant compounds. Thus, the therapeutic agent may be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent such as streptokinase and tissue plasminogen activator, an antigen, a hormone, a growth factor, a ribozyme, a retroviral vector, an anti-proliferative agent such as rapamycin (sirolimus), 40-O-(2-hydroxyethyl)rapamycin (everolimus), 40-O-(3-hydroxypropyl)rapamycin, 40-O-(2-hydroxyethoxy)ethylrapamycin, 40-O-tetrazolylrapamycin, 40-epi(N1-tetrazolyl) rapamycin (zotarolimus, ABT-578), paclitaxel, docetaxel, methotrexate, azathioprine, vincristine, vinblastine, fluorouracil, doxorubicin hydrochloride, and mitomycin, an antiplatelet compound, an anticoagulant, an antifibrin, an antithrombins such as sodium heparin, a low molecular weight heparin, a heparinoid, hirudin, argatroban, forskolin, vapiprost, prostacyclin, a prostacyclin analogue, dextran, D-phe-pro-arg-chloromethylketone (synthetic antithrombin), dipyridamole, glycoprotein IIb/IIIa platelet membrane receptor antagonist antibody, recombinant hirudin, a thrombin inhibitor such as Angiomax ä, a calcium channel blocker such as nifedipine, colchicine, a fibroblast growth factor (FGF) antagonist, fish oil (omega 3-fatty acid), a histamine antagonist, lovastatin, a monoclonal antibodie, nitroprusside, a phosphodiesterase inhibitor, a prostaglandin inhibitor, suramin, a serotonin blocker, a steroid, a thioprotease inhibitor, triazolopyrimidine, a nitric oxide or nitric oxide donor, a super oxide dismutase, a super oxide dismutase mimetic, estradiol, an anticancer agent, a dietary supplement such as vitamins, an anti-inflammatory agent such as aspirin, tacrolimus, dexamethasone and clobetasol, a cytostatic substance such as angiopeptin, an angiotensin converting enzyme inhibitor such as captopril, cilazapril or lisinopril, an antiallergic agent such as permirolast potassium, alpha-interferon, bioactive RGD, and genetically engineered epithelial cells. Other therapeutic agents which are currently available or that may be developed in the future for use with implantable medical devices may likewise be used and all are within the scope of this invention.

Presently preferred therapeutic agents for use with this invention are rapamycin (sirolimus), 40-O-(2-hydroxyethyl) rapamycin (everolimus), 40-O-(3-hydroxypropyl)rapamycin, 40-O-(2-hydroxyethoxy)ethylrapamcyin, 40-O-tetrazolylrapamycin and 40-epi(N1-tetrazolyl)rapamycin (zotarolimus, ABT-578).

What is claimed is:

1. A poly(ester-amide) having the formula:

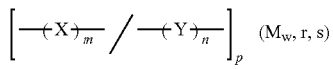

wherein:
m is an integer from 0 to about 200;
n is an integer from 0 to about 200;
p is an integer from 1 to about 3000;
$M_n$ is from about 10,000 to about 1,000,000 Da.
s is a number from 0 to 1, inclusive;
t is a number from 0 to 1, inclusive;
s+t=1;
X has the chemical structure:

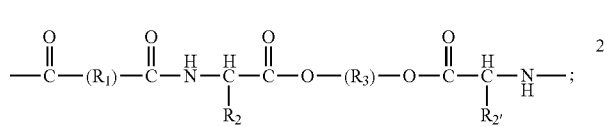

Y has the chemical structure:

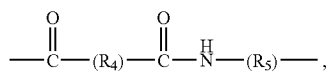

wherein:
$R_5$ is selected from the group consisting of:

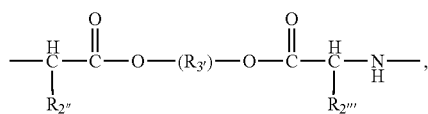

$-CH(COR_6)CH_2S-$, $-CH(COR_6)CH_2O-$, $-CH(COR_6)(CH_2)_4NH-$, $-(CH_2)_4CH(COR_6)NH-$, $-CH(COR_6)CH(CH_3)O-$,

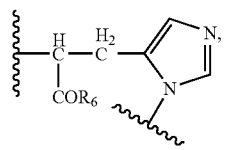

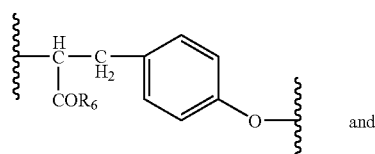

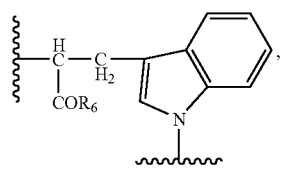

wherein:
$R_6$ is selected from the group consisting of —OH, —O(1C-20C)alkyl, —O(1C-20C)alkenyl and —O($CH_2CH_2O$)$_q$$CH_2CH_2OR_7$, wherein:
q is an integer from 1 to 600, inclusive;
$R_7$ is selected from the group consisting of hydrogen, $-C(O)CH=CH_2$ and $-C(O)C(CH_3)=CH_2$;
$R_1$ and $R_4$ are independently selected from the group consisting of (1C-12C)alkyl and (2C-12C)alkenyl;
$R_2$, $R_{2'}$, $R_{2''}$ and $R_{2'''}$ are independently selected from the group consisting of hydrogen and (1C-4C)alkyl, wherein:
the alkyl group is optionally substituted with a moiety selected from the group consisting of —OH, —SH, —SeH, —C(O)OH, —NHC(NH)$NH_2$,

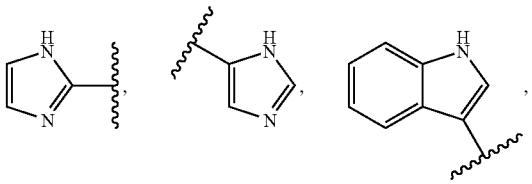

phenyl and

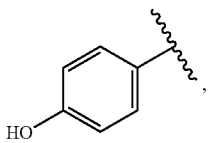

or
one or more of $R_2$, $R_{2'}$, $R_{2''}$ and $R_{2'''}$ may form a bridge between the carbon to which it is attached and the adjacent nitrogen, the bridge comprising $-CH_2CH_2CH_2-$;
$R_3$ and $R_{3'}$ are independently selected from the group consisting of (1C-12C)alkyl, (2C-12C)alkenyl, (3C-8C)cycloalkyl and $-(CH_2CH_2O)_qCH_2CH_2-$, wherein q is an integer from 1 to 10, inclusive,
wherein the poly(ester-amide) is from about 0.05 mol % to about 5 mol % cross-linked.

2. The poly(ester-amide) of claim 1, wherein $M_n$ is from about 20,000 Da to about 500,000 Da.

3. The poly(ester-amide) of claim 1, wherein the crosslink is a chemical crosslink.

4. The poly(ester-amide) of claim 3, wherein the chemical crosslink comprises a reaction product of an —OH, —SH, —$NH_2$ or —C(O)OH substituent on $R_2$, $R_{2'}$, $R_{2''}$, $R_{2'''}$ or $R_6$ with a multifunctional OH-reactive, —SH-reactive, —$NH_2$-reactive or —C(O)OH-reactive multifunctional crosslinking agent.

5. The poly(ester-amide) of claim 4, wherein the OH-reactive, —SH-reactive, —$NH_2$-reactive or —C(O)OH-reactive multifunctional crosslinking agent comprises a diisocyanate.

6. The poly(ester-amide) of claim 5, wherein the diisocyanate is selected from the group consisting of 1,2-ethanediisocyanate, 1,3-propanediisocyanate, 1,4-butanediisocyanate, 1,5-pentanediisocyanate, lysine diisocyanate and 1,4-cyclohexanediisocyanate.

7. The poly(ester-amide) of claim 4, wherein the —SH-reactive multifunctional crosslinking agent comprises a bismaleimide.

8. The poly(ester-amide) of claim 4, wherein the —OH-reactive, —SH-reactive, NH$_2$-reactive or —C(O)OH-reactive multifunctional crosslinking agent comprises a diepoxide.

9. The poly(ester-amide) of claim 4, wherein the —OH-reactive, —SH-reactive, —NH$_2$-reactive or —C(O)OH-reactive multifunctional crosslinking agent comprises a diisothiocyanate.

10. The poly(ester-amide) of claim 4, wherein the —OH-reactive, —SH-reactive, —NH$_2$-reactive or —C(O)OH-reactive multifunctional crosslinking agent comprises a diacid halide.

11. The poly(ester-amide) of claim 5, wherein:

$R_2$, $R_{2'}$, $R_{2''}$, and $R_{2'''}$ are independently selected from the group consisting of unsubstituted (1C-4C)alkyl and a bridge between the carbon to which it is attached and the adjacent nitrogen, the bridge comprising —CH$_2$CH$_2$CH$_2$—;

$R_5$ is selected from the group consisting of —CH(COR$_6$)CH$_2$S—, —CH(COR$_6$)CH$_2$O—, —CH(COR$_6$)(CH$_2$)$_4$NH—, —(CH$_2$)$_4$CH(COR$_6$)NH—, —CH(COR$_6$)CH(CH$_3$)O—,

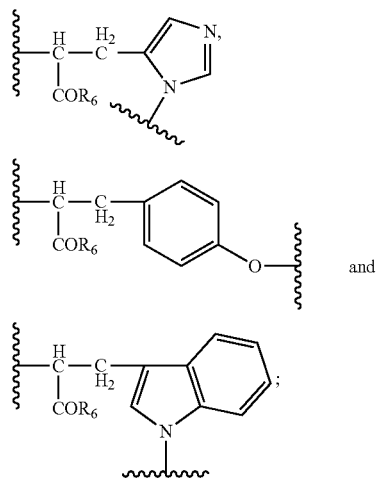

and $R_6$ is —OH.

12. The poly(ester-amide) of claim 11, wherein $R_5$ is —(CH$_2$)$_4$CH(COR$_6$)NH—.

13. The poly(ester-amide) of claim 12, wherein $R_2$ and $R_{2'}$ are —CH$_2$CH(CH$_3$)$_2$.

14. The poly(ester-amide) of claim 4, wherein the OH-reactive, SH-reactive, NH$_2$ reactive, C(O)OH-reactive multifunctional crosslinking agent is a multifunctional aziridine compound.

15. The poly(ester-amide) of claim 14, wherein the multifunctional aziridine compound is pentaerythriol tris(3-aziridinopropionate).

16. The poly(ester-amide) of claim 15, wherein:

$R_2$, $R_{2'}$, $R_{2''}$, and $R_{2'''}$ are independently selected from the group consisting of unsubstituted (1C-4C)alkyl and a bridge between the carbon to which it is attached and the adjacent nitrogen, the bridge comprising —CH$_2$CH$_2$CH$_2$—;

$R_5$ is selected from the group consisting of —CH(COR$_6$)CH$_2$S—, —CH(COR$_6$)CH$_2$O—, —CH(COR$_6$)(CH$_2$)$_4$NH—, —(CH$_2$)$_4$CH(COR$_6$)NH—, —CH(COR$_6$)CH(CH$_3$)O—,

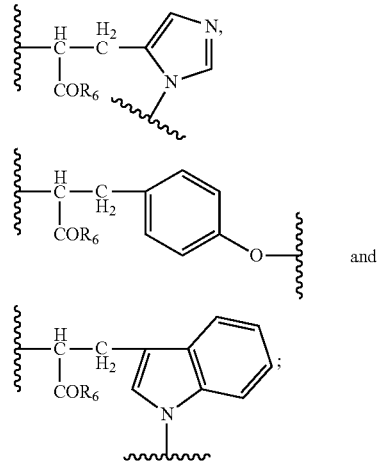

$R_6$ is —OH.

17. The poly(ester-amide) of claim 16, wherein $R_5$ is —(CH$_2$)$_4$CH(COR$_6$)NH—.

18. The poly(ester-amide) of claim 17, wherein $R_2$ and $R_{2'}$ are —CH$_2$CH(CH$_3$)$_2$.

19. The poly(ester-amide of claim 18, wherein:

$R_1$ and $R_4$ are —(CH$_2$)$_8$; and, $R_3$ is —(CH$_2$)$_6$—.

20. The poly(ester-amide) of claim 3, wherein:

$R_5$ is selected from the group consisting of —CH(COR$_6$)CH$_2$S—, —CH(COR$_6$)CH$_2$O—, —CH(COR$_6$)(CH$_2$)$_4$NH—, —(CH$_2$)$_4$CH(COR$_6$)NH—, —CH(COR$_6$)CH(CH$_3$)O—,

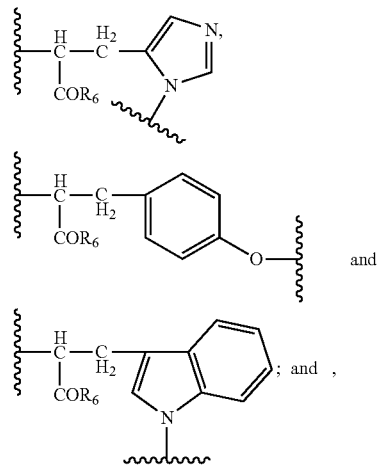

$R_6$ is selected from the group consisting of –O(1C-20C)alkenyl and —O(CH$_2$CH$_2$O)$_q$CH$_2$CH$_2$OR$_7$, wherein:

q is an integer from 0 to 600, inclusive;

$R_7$ is selected from the group consisting of —C(O)CH=CH$_2$ and —C(O)C(CH$_3$)=CH$_2$; and, the chemical crosslink comprises UV or free-radical initiated reaction of the double bond.

21. The poly(ester-amide) of claim 20, wherein $R_5$ is —(CH$_2$)$_4$CH(COR$_6$)NH—.

22. The poly(ester-amide) of claim 21, wherein $R_6$ is selected from the group consisting of —O(CH$_2$)$_8$CH=CH(CH$_2$)$_7$CH$_3$ and

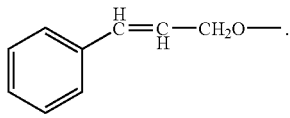

23. The poly(ester-amide) of claim 22, wherein:
$R_1$ and $R_4$ are —(CH$_2$)$_8$—;
$R_2$ and $R_{2'}$ are —CH$_2$CH(CH$_3$)$_2$; and,
$R_3$ is —(CH$_2$)$_6$.
24. The poly(ester-amide) of claim 3, wherein:
$R_5$ is

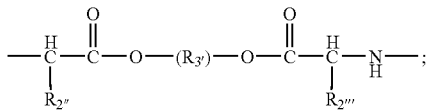

one of $R_1$ or $R_4$ is a (2C-12C)alkyenyl, the other is a (1C-12C)alkyl; or,
$R_1$ and $R_4$ are a (2C-12C)alkyenyl; and,
the chemical crosslink comprises UV or free-radical initiated reaction of the alkenyl double bond.
25. The poly(ester-amide) of claim 3, wherein:
n is 0;
$R_1$ is a (2C-12C)alkyenyl; and,
the chemical crosslink comprises UV or free-radical initiated reaction of the alkenyl double bond.
26. The poly(ester-amide) of claim 25, wherein:
$R_2$ and $R_{2'}$ are —(CH$_2$)CH(CH$_3$)$_2$; and,
$R_3$ is —(CH$_2$)$_6$—.
27. The poly(ester-amide) of claim 3, wherein:
at least one of $R_2$, $R_{2'}$, $R_{2''}$, $R_{2'''}$ and $R_6$ comprises a —C(O)OH group; and
the chemical crosslink comprises an ionomer.
28. The poly(ester-amide) of claim 27, wherein the ionomer comprises a monovalent cation.
29. The poly(ester-amide) of claim 28, wherein the monovalent cation is selected from the group consisting of sodium, potassium, lithium and silver.
30. The poly(ester-amide) or claim 27, wherein the ionomer comprises a polyvalent cation.
31. The polyester-amide) of claim 30, wherein the polyvalent cation is selected from the group consisting of calcium (II), magnesium(II), zinc(II), iron(II) and aluminum(III).
32. The poly(ester-amide) of claim 27, wherein:
$R_2$ and $R_{2'}$ are independently selected from the group consisting of hydrogen and (1C-4C)alkyl;
$R_5$ is selected from the group consisting of —CH(COR$_6$)CH$_2$S—, —CH(COR$_6$)CH$_2$O—, —CH(COR$_6$)(CH$_2$)$_4$NH—, —(CH$_2$)$_4$CH(COR$_6$)NH—, —CH(COR$_6$)CH(CH$_3$)O—,

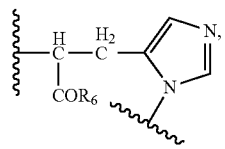

-continued

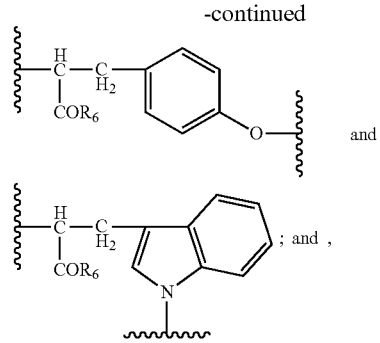

$R_6$ is —OH.
33. The poly(ester-amide) of claim 32, wherein:
$R_2$ and $R_{2'}$ are —CH$_2$CH(CH$_3$)$_2$; and,
$R_5$ is —(CH$_2$)$_4$CH(COR$_6$)NH—.
34. The poly(ester-amide) of claim 33, wherein:
$R_1$ and $R_4$ are —(CH$_2$)$_8$—; and,
$R_3$ is —(CH$_2$)$_6$—.
35. The poly(ester-amide) of claim 34, wherein the ionomer comprises Zn(II).
36. The poly(ester-amide) of claim 1, wherein the crosslink is a physical crosslink.
37. The poly(ester-amide) of claim 36, wherein:
A is a soft segment;
B is a hard segment; and,
the physical crosslink comprises segregated domains of soft segments and paracrystalline hard segments.
38. The poly(ester-amide) of claim 37, wherein:
A has a glass-transition temperature of 40° C. of lower; and,
B has a glass transition temperature of 45° C. or higher.
39. The poly(ester-amide) of claim 38, wherein:
$R_5$ is

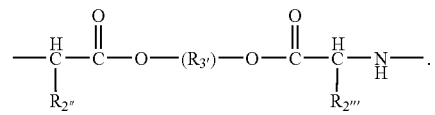

40. The poly(ester-amide) of claim 39, wherein:
$R_1$ is —(CH$_2$)$_8$—;
$R_2$ and $R_{2'}$ are —(CH(CH$_3$)CH$_2$CH$_3$;
$R_3$ is —(CH$_2$)$_6$—
$R_{1'}$ is —(CH$_2$)$_4$—;
$R_{2''}$ and $R_{2'''}$ are —CH(CH$_3$)$_2$; and,
$R_{3'}$ is —(CH$_2$)$_3$—.
41. The poly(ester-amide) of claim 39, wherein:
$R_1$ is —(CH$_2$)$_4$—;
$R_2$ and $R_{2'}$ are —(CH(CH$_3$)CH$_2$CH$_3$;
$R_3$ is —(CH$_2$)$_{12}$—
$R_{1'}$ is —(CH$_2$)$_4$—;
$R_{2''}$ and $R_{2'''}$ are —CH(CH$_3$)$_2$; and,
$R_{3'}$ is —(CH$_2$)$_3$—.
42. The poly(ester-amide) of claim 39, wherein:
$R_1$ is —(CH$_2$)$_8$—;
$R_2$, $R_{2'}$, $R_{2''}$ and $R_{2'''}$ are —(CH(CH$_3$)CH$_2$CH$_3$;
$R_3$ is —(CH$_2$)$_6$—;
$R_{1'}$ is —(CH$_2$)$_2$—; and,
$R_{3'}$ is —(CH$_2$)$_2$—.

43. The poly(ester-amide) of claim 36, wherein:
A is amorphous;
B is crystalline; and,
the crosslink comprises inter-chain crystallization.
44. The poly(ester-amide) of claim 43, wherein:
$R_5$ is
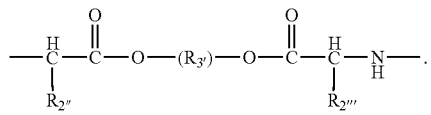
45. The poly(ester-amide) of claim 44, wherein:
$R_1$ is —$(CH_2)_8$—;
$R_{1'}$ is —$(CH_2)_4$;
$R_2$ and $R_{2'}$ are —$CH_2CH(CH_3)_2$;
$R_{2''}$ and $R_{2'''}$ are —$CH_2$phenyl;
$R_3$ is —$(CH_2)_6$—; and,
$R_{3'}$ is —$(CH_2)_4$—.
* * * * *